US007358364B2

(12) United States Patent
Van Zandt et al.

(10) Patent No.: US 7,358,364 B2
(45) Date of Patent: Apr. 15, 2008

(54) SUBSTITUTED CARBOXYLIC ACIDS

(75) Inventors: Michael C. Van Zandt, Guilford, CT (US); Darren Whitehouse, Westbrook, CT (US); Kerry Combs, Wallingford, CT (US); Shaojing Hu, Hamden, CT (US)

(73) Assignee: The Institute for Pharmaceutical Discovery LLC, Branford, CT (US)

( * ) Notice: Subject to any disclaimer, the term of this patent is extended or adjusted under 35 U.S.C. 154(b) by 531 days.

(21) Appl. No.: 10/823,842

(22) Filed: Apr. 14, 2004

(65) Prior Publication Data

US 2004/0266788 A1 Dec. 30, 2004

Related U.S. Application Data

(60) Provisional application No. 60/467,057, filed on Apr. 30, 2003.

(51) Int. Cl.
*C07D 471/00* (2006.01)
*C07D 498/00* (2006.01)
*C07D 513/00* (2006.01)
*C07D 405/00* (2006.01)
*C07D 307/87* (2006.01)

(52) U.S. Cl. .......................... 546/85; 546/86; 546/87; 546/112; 548/454; 548/465; 548/491; 549/460

(58) Field of Classification Search ............... 548/490, 548/491, 454, 465, 482; 546/85, 86, 87, 546/112; 549/460, 461
See application file for complete search history.

(56) References Cited

U.S. PATENT DOCUMENTS

| | | | |
|---|---|---|---|
| 3,755,603 A | 8/1973 | Fried et al. | |
| 3,859,338 A | 1/1975 | Engel et al. | |
| 4,072,754 A * | 2/1978 | Schacht et al. ............. | 514/510 |
| 5,886,022 A | 3/1999 | Schneider et al. | |
| 6,207,698 B1 | 3/2001 | Wantanabe et al. | |
| 6,214,877 B1 | 4/2001 | Havran et al. | |
| 6,214,991 B1 | 4/2001 | Jones et al. | |
| 6,221,902 B1 | 4/2001 | Malamas et al. | |
| 6,232,322 B1 * | 5/2001 | Malamas et al. ........... | 514/303 |
| 6,420,426 B1 | 7/2002 | Van Zandt | |
| 7,163,952 B2 | 1/2007 | Inaba et al. | |
| 2002/0077347 A1 | 6/2002 | Liu et al. | |

FOREIGN PATENT DOCUMENTS

| | | |
|---|---|---|
| DE | 19 28 438 | 12/1969 |
| DE | 2307038 * | 2/1973 |
| DE | 101 50 172 | 4/2003 |
| EP | 0 020 230 | 12/1980 |
| EP | 0 612 743 | 8/1994 |
| EP | 0 950 656 | 10/1999 |
| EP | 1704856 | 9/2006 |
| GB | 1 176 339 | 1/1970 |
| GB | 1 209 538 | 10/1970 |
| GB | 1 249 492 | 10/1971 |
| WO | WO 96/15096 | 5/1996 |
| WO | WO 97/38986 | 10/1997 |
| WO | WO 97/39748 | 10/1997 |
| WO | WO 99/11255 | 3/1999 |
| WO | WO 99/32466 | 7/1999 |
| WO | WO 99/46236 | 9/1999 |
| WO | 6658518 * | 11/1999 |
| WO | WO 99/58514 | 11/1999 |
| WO | WO 99/58520 | 11/1999 |
| WO | WO 00/64888 | 11/2000 |
| WO | WO 01/70753 | 9/2001 |
| WO | WO 01/83461 | 11/2001 |
| WO | WO 01/83464 | 11/2001 |
| WO | WO 02/04459 | 1/2002 |
| WO | WO 02/08188 | 1/2002 |
| WO | WO 02/28844 | 4/2002 |
| WO | WO 02/100341 | 12/2002 |
| WO | 1288199 | 3/2003 |
| WO | WO 03/035610 | 5/2003 |
| WO | WO 2004/010992 | 2/2004 |
| WO | WO 2004/020409 | 3/2004 |
| WO | WO 02/064094 | 8/2004 |
| WO | WO 2004/092146 | 10/2004 |
| WO | WO 2004/099168 | 11/2004 |
| WO | WO 2006/050097 | 5/2006 |

OTHER PUBLICATIONS

Mrphy et al., Bioorganic & Medicinal Chemistry, "3D-QSAR CoMFA and CoMSIA on protein Tyrosine phosphate 1B inhibitors", vol. 10, 2002, pp. 2267-2282.*

(Continued)

*Primary Examiner*—Margaret D. Seaman
*Assistant Examiner*—Niloofar Rahmani
(74) *Attorney, Agent, or Firm*—McDonnell Boehnen Hulbert & Berghoff LLP

(57) ABSTRACT

The present invention relates to compounds and pharmaceutically acceptable salts of formula (I):

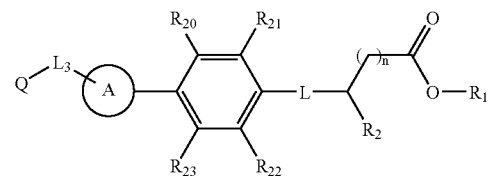

which are useful in the treatment of metabolic disorders related to insulin resistance or hyperglycemia. These compounds include inhibitors of protein tyrosine phosphatase (PTP-1B) that are useful in the treatment of diabetes and other PTP-1B mediated diseases, such as cancer, neurodegenerative diseases and the like. The compounds of the invention are also useful in pharmaceutical compositions and methods of treating the aforementioned conditions.

11 Claims, No Drawings

OTHER PUBLICATIONS

Malamas et al., J. Med. Chem. "Novel benzofuran and benzothiophene biphenyls as inhibitors of protein tyrosine phosphate 1B with antihyperglycemic properties", 2000, vol. 43, pp. 1293-1310.*

International Search Report PCT/US2004/011371 (WO 2004/099168) date of publication of International Search Report Feb. 24, 2005.

Cousse, et al.; Synthèse, structure, et activité hypocholestérolémiante d'une série d'acides gamma-aryl, gamma-oxo butyriques substitutés et dérivés; Eur. J. Med. Chem., vol. 22, 45-57 (1987).

Database Caplus [Online], Chemical Abstracts Service, Columbus, Ohio, US, Chanal, J.L. et al., Comparison of the Metabolism and Pharmacokinetics of Metbufen and Itanoxone and their Analogs in Rats, XP002373400, Database Accession No. 1989 :275 abstract.

Campo, M.A. et al., Novel 1,4-Palladium Migration in Organopalladium Intermediates Derived from o-Iodobiaryls, Journal of the American Chemical Society, vol. 124, No. 48, 2002, pp. 14326-14327.

Summers, J.B. et al., Hydroxamic Acid Inhibitors 5-Lipoxygenase, J. Med. Chem., vol. 30, No. 3, 1987, pp. 574-580.

Database Crossfire Beilstein, Beilstein Institut Zur Forderung der Chemischen Wissenschaften, Frankfurt am Main, DE ; XP002373401, Database Accession No. BRN 1955124 abstract.

Database Crossfire Beilstein, Beilstein Institut Zur Forderung der Chemischen Wissenschaften, Frankfurt am Main, DE ; XP002373402, Database Accession No. BRN 2358371 abstract.

Database Crossfire Beilstein, Beilstein Institut Zur Forderung der Chemischen Wissenschaften, Frankfurt am Main, DE ; XP002373403, Database Accession No. BRN 9931315, 9943434 abstract.

Database Crossfire Beilstein, Beilstein Institut Zur Forderung der Chemischen Wissenschaften, Frankfurt am Main, DE ; XP002371579, Database Accession No. BRN 224657 abstract.

Database Crossfire Beilstein, Beilstein Institut Zur Forderung der Chemischen Wissenschaften, Frankfurt am Main, DE ; XP002371580, Database Accession No. BRN 22403 abstract.

Database Crossfire Beilstein, Beilstein Institut Zur Forderung der Chemischen Wissenschaften, Frankfurt am Main, DE ; XP002371581, Database Accession No. BRN 1965282 abstract.

Database Crossfire Beilstein, Beilstein Institut Zur Forderung der Chemischen Wissenschaften, Frankfurt am Main, DE ; XP002371587, Database Accession No. BRN 983606 abstract.

Database Crossfire Beilstein, Beilstein Institut Zur Forderung der Chemischen Wissenschaften, Frankfurt am Main, DE ; XP002371589, Database Accession No. BRN 1307336 abstract.

Database Crossfire Beilstein, Beilstein Institut Zur Forderung der Chemischen Wissenschaften, Frankfurt am Main, DE ; XP002373404, Database Accession No. BRN 2811320 abstract.

Database Crossfire Beilstein, Beilstein Institut Zur Forderung der Chemischen Wissenschaften, Frankfurt am Main, DE ; XP002373405, Database Accession No. BRN 2468213 abstract.

Database Crossfire Beilstein, Beilstein Institut Zur Forderung der Chemischen Wissenschaften, Frankfurt am Main, DE ; XP002373406, Database Accession No. BRN 2378427 abstract.

Schwab, J.M. et al., Absolute Configuration of an Allenic Enzyme Inactivator, Tetrahedron Letters., vol. 25. No. 43, 1984, pp. 4909-4912.

Database Caplus [Online], Chemical Abstracts Service, Columbus, Ohio, US ; Tajima, Hisao et al., Preparation of Phenylalkanoic Acid Derivatives as Peroxisome Proliferator-Activated Receptor Controllers, XP002371578, retrieved from STN, Database Accession No. 1999:184126 abstract.

Bouchain G. et al., Development of Potential Antitumor Agents. Synthesis and Biological Evaluation of a New Set of Sulfonamide Derivcatives as Histone Deacetylase Inhibitors, Journal of Medicinal Chemistry, American Chemical Society, vol. 46, 2003, pp. 820-830.

Leone-Bay A. et al., 4-[4-[(2-Hydroxybenzoyl) Aminophenylbutyri C Acid as a Novel Oral Delivery Agent for Recombinant Human Growth Hormone, Journal of Medicinal Chemistry, American Chemical Society, vol. 39, Jun. 21, 1996, pp. 2571-2578.

Astles, Peter C., et al., Selective Endothelin A Receptor Antagonists. 4. Discovery and Structure-Activity Relationships of Stilbene Acid and Alcohol Derivatives, Journal of Medicinal Chemistry, vol. 41, No. 15, 1998, pp. 2745-2753.

A. Bapna et al., Polymer-Assisted, Multi-Step Solution Phase Synthesis and Biological Screening of Histone Deacetylase Inhibitors, Org. Biomol. Chem., vol. 2, No. 4, 2004, pp. 611-620.

R. Lavoie et al., Design and Synthesis of a Novel Class of Histone Deacetylase Inhibitors, Bioorg. Med. Chem., vol. 11, No. 21, 2001, pp. 2847-2850.

Database Caplus [Online], Chemical Abstracts Service, Columbus, Ohio, US, Kitamura, Yushi et al., Hsp90 Family Protein Inhibotors, XP002371590, retrieved from STN, Database Accession No. 2002 :612072 abstract.

Database Crossfire Beilstein, Beilstein Institut Zur Forderung der Chemischen Wissenschaften, Frankfurt am Main, DE ; XP002371582, Database Accession No. BRN 1982968 abstract.

Database Crossfire Beilstein, Beilstein Institut Zur Forderung der Chemischen Wissenschaften, Frankfurt am Main, DE ; XP002371583, Database Accession No. BRN 194268, 119245 abstract.

Database Crossfire Beilstein, Beilstein Institut Zur Forderung der Chemischen Wissenschaften, Frankfurt am Main, DE ; XP002371584, Database Accession No. BRN 3103769 abstract.

Database Crossfire Beilstein, Beilstein Institut Zur Forderung der Chemischen Wissenschaften, Frankfurt am Main, DE ; XP003371585, Database Accession No. BRN 3409899 abstract.

Database Crossfire Beilstein, Beilstein Institut Zur Forderung der Chemischen Wissenschaften, Frankfurt am Main, DE ; XP002371586, Database Accession No. BRN 842302 abstract.

Database Crossfire Beilstein, Beilstein Institut Zur Forderung der Chemischen Wissenschaften, Frankfurt am Main, DE ; XP002371588, Database Accession No. BRN. 13930 abstract.

* cited by examiner

SUBSTITUTED CARBOXYLIC ACIDS

BACKGROUND OF THE INVENTION

1. Field of the Invention

The invention relates to substituted carboxylic acids and more specifically to such compounds that are useful in the treatment of diabetes. More specifically, it relates to such compounds that are capable of inhibiting Protein tyrosine phosphatase-1B (PTP-1B), which is a negative regulator of the insulin signaling pathway, and improves insulin-sensitivity.

2. Description of the Related Art

Protein tyrosine phosphatases are a large family of transmembrane or intracellular enzymes that dephosphorylate substrates involved in a variety of regulatory processes (Fischer et al., 1991, Science 253:401-406). Protein tyrosine phosphatase-1B (PTP-1B) is an approximately 50 kd intracellular protein, which is present in abundant amounts in various human tissues (Charbonneau et al., 1989, Proc. Natl. Acad. Sci. USA 86:5252-5256; Goldstein, 1993, Receptor 3:1-15).

Determining which proteins are substrates of PTP-1B has been of considerable interest. One substrate which has aroused especial interest is the insulin receptor. The binding of insulin to its receptor results in autophosphorylation of the domain. This causes activation of the insulin receptor tyrosine kinase, which phosphorylates the various insulin receptor substrate (IRS) proteins that propagate the insulin signaling event further downstream to mediate insulin's various biological effects.

Seely et al., 1996, Diabetes 45:1379-1385 ("Seely") studied the relationship of PTP-1B and the insulin receptor in vitro. Seely constructed a glutathione S-transferase (GST) fusion protein of PTP-1B that had a point mutation in the PTP-1B catalytic domain. Although catalytically inactive, this fusion protein was able to bind to the insulin receptor, as demonstrated by its ability to precipitate the insulin receptor from purified receptor preparations and from whole cell lysates derived from cells expressing the insulin receptor.

Ahmad et al., 1995, J. Biol. Chem. 270:20503-20508 used osmotic loading to introduce PTP-1B neutralizing antibodies into rat KRC-7 hepatoma cells. The presence of the antibody in the cells resulted in an increase of 42% and 38%, respectively, in insulin stimulated DNA synthesis and phosphatidyinositol 3' kinase activity. Insulin receptor autophosphorylation and insulin receptor substrate-1 tyrosine phosphorylation were increased 2.2 and 2.0-fold, respectively, in the antibody-loaded cells. The antibody-loaded cells also showed a 57% increase in insulin stimulated insulin receptor kinase activity toward exogenous peptide substrates.

Kennedy et al., 1999, Science 283: 1544-1548 showed that protein tyrosine phosphatase PTP-1B is a negative regulator of the insulin signaling pathway, indicating that inhibitors of this enzyme are beneficial in the treatment of Type 2 diabetes, which appears to involve a defect in an early process in insulin signal transduction rather than a structural defect in the insulin receptor itself. (J. M. Olefsky, W. T. Garvey, R. R. Henry, D. Brillon, S. Matthai and G. R. Freidenberg, G. R. (1988).) Cellular mechanisms of insulin resistance in non-insulin-dependent (Type II) diabetes. (Am. J. Med. 85: Suppl. 5A, 86-105.) A drug that improved insulin sensitivity would have several advantages over traditional therapy of NIDDM using sulfonylureas, which do not alleviate insulin resistance but instead compensate by increasing insulin secretion.

Therefore, inhibitors of PTP-1B are useful in controlling or treating Type 2 diabetes, in improving glucose tolerance, and in improving insulin sensitivity in patients in need thereof.

The compounds are also useful in treating or controlling other PTP-1B mediated diseases, such as the treatment of cancer, neurodegenerative diseases and the like.

SUMMARY OF THE INVENTION

In a broad aspect, the invention encompasses the compounds of formula (I) shown below, pharmaceutical compositions containing the compounds and methods employing such compounds or compositions in the treatment of diabetes.

In one aspect, the invention encompasses compounds of formula I:

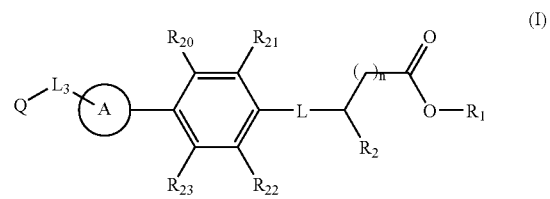

and pharmaceutically acceptable salts thereof, wherein n is 0, 1, 2, 3, or 4;

$R_1$ is H, $C_1$-$C_6$ alkyl, phenyl($C_1$-$C_6$)alkyl, or $C_3$-$C_6$ alkenyl;

$R_2$ is phenyl, phenyl($C_1$-$C_4$) alkyl, $C_1$-$C_6$ alkyl, —($C_1$-$C_4$) alkyl-C(O)NH$_2$, —($C_1$-$C_4$) alkyl-C(O)NH($C_1$-$C_4$)alkyl, —($C_1$-$C_4$) alkyl-C(O)N($C_1$-$C_4$)alkyl($C_1$-$C_4$)alkyl, —($C_1$-$C_4$) alkyl-S(O)$_b$—($C_1$-$C_4$) alkyl, ($C_1$-$C_4$) hydroxyalkyl, —($C_1$-$C_4$) alkyl-heterocycloalkyl, wherein the heterocycloalkyl group is optionally fused to a phenyl ring and wherein the heterocycloalkyl portion, the phenyl portion, or both are optionally substituted with a total of 1, 2, 3, or 4 groups that are independently halogen, $C_1$-$C_4$ alkyl, $C_1$-$C_4$ alkoxy, —SO$_2$—($C_1$-$C_4$) alkyl, haloalkyl, or haloalkoxy;

wherein b is 0, 1, or 2;

$R_{20}$, $R_{21}$, $R_{22}$, and $R_{23}$ are independently selected from H, arylalkoxy, arylalkyl, halogen, alkyl, haloalkyl, OH, alkoxy, NO$_2$, NH$_2$, NH($C_1$-$C_6$)alkyl, N($C_1$-$C_6$alkyl) ($C_1$-$C_6$alkyl), NH-aryl, NHC(O)—($C_1$-$C_4$) alkyl-aryl, N($C_1$-$C_4$ alkyl)C(O)—($C_1$-$C_4$)alkyl-aryl, N($C_1$-$C_4$)alkyl-aryl, —NHSO$_2$-aryl, —N($C_1$-$C_4$alkyl)SO$_2$aryl, wherein the aryl group is optionally substituted with 1, 2, 3, or 4 groups that are independently $C_1$-$C_6$ alkyl, $C_1$-$C_6$ alkoxy, halogen, OH, NO$_2$, haloalkyl, haloalkoxy;

L is —SO$_2$NH—, —SO$_2$N($C_1$-$C_4$) alkyl-, —NHSO$_2$—, —N($C_1$-$C_4$ alkyl)SO$_2$—, O, —C(O)NH—, —C(O)N($C_1$-$C_4$)alkyl-, —SO$_2$—, —C(O)—($C_1$-$C_4$) alkyl-, —($C_1$-$C_4$) alkyl-C(O)—, —NH—, —($C_1$-$C_6$ alkyl)-O—N=, or —N($C_1$-$C_4$ alkyl)-, wherein the alkyl group is optionally substituted with phenyl, wherein the phenyl is optionally substituted with 1, 2, 3, or 4 groups that are independently $C_1$-$C_6$ alkyl, $C_1$-$C_6$ alkoxy, halogen, OH, NO$_2$, haloalkyl, or haloalkoxy;

$L_3$ is a bond, absent, —($C_1$-$C_4$)alkyl-O—, —O—($C_1$-$C_4$) alkyl, —($C_1$-$C_4$) alkyl-, —C(O)—, —C(O)NH—, or —C(O)N($C_1$-$C_4$ alkyl)-;

the A-ring is aryl selected from the group consisting of phenyl, naphthyl and fluorenyl, or heteroaryl, each of which is optionally substituted with 1, 2, or 3 groups that are independently, halogen, $C_1$-$C_4$ alkyl, $C_1$-$C_4$ alkoxy, $C_1$-$C_4$ haloalkyl, $C_1$-$C_4$ haloalkoxy, $NO_2$, $NH_2$, $NH(C_1$-$C_6)$alkyl, $N(C_1$-$C_6)$ alkyl $(C_1$-$C_6)$ alkyl;

Q is H, aryl, heteroaryl, -heteroaryl-alkyl, -aryl-heteroaryl, aryl-C(O)-aryl, aryl-($C_1$-$C_4$ alkyl)-aryl, heteroaryl-($C_1$-$C_4$ alkyl)-aryl, -heteroaryl-aryl, wherein the aryl group is a phenyl, naphthyl, or fluorenyl, each of which is optionally substituted with 1, 2, 3, or 4 groups that are independently $C_1$-$C_6$ alkyl, $C_1$-$C_4$ alkoxycarbonyl, $C_1$-$C_6$ alkoxy, halogen, haloalkyl, haloalkoxy, $NR_6R_7$, or phenyl;

wherein
$R_6$ and $R_7$ are independently H, $C_1$-$C_6$ alkyl, aryl($C_1$-$C_6$) alkyl, alkanoyl, arylalkanoyl, alkoxycarbonyl, arylalkoxycarbonyl, heteroarylcarbonyl, heteroaryl, heterocycloalkylcarbonyl, —C(O)$NH_2$, —C(O)NH($C_1$-$C_6$) alkyl, —C(O)N($C_0$-$C_6$)alkyl($C_1$-$C_6$)alkyl, or —$SO_2$-aryl, wherein the cyclic groups are optionally substituted with 1, 2, 3, or 4 groups that are independently halogen, $C_1$-$C_4$ alkyl, $C_1$-$C_4$ alkoxy, $NO_2$, OH, $NH_2$, NH($C_1$-$C_6$)alkyl, N($C_1$-$C_6$)alkyl($C_1$-$C_6$)alkyl, haloalkyl or haloalkoxy.

Compounds of formula I bind to PTP-1B. Preferably that interaction results in inhibition of the enzyme.

The invention also includes intermediates that are useful in making the compounds of the invention.

The invention also provides pharmaceutical compositions comprising a compound or salt of formula I and at least one pharmaceutically acceptable carrier, solvent, adjuvant or diluent.

The invention further provides methods of treating disease in a patient in need of such treatment, comprising administering a compound or pharmaceutically acceptable salt of formula I, or a pharmaceutical composition comprising a compound or salt of formula I.

In another aspect, the invention provides a method for inhibiting protein tyrosine phosphatase comprising administering a therapeutically effective amount of a compound of formula I.

In another aspect, the invention provides a method for treating metabolic disorders related to insulin resistance or hyperglycemia, comprising administering a therapeutically effective amount of a compound of formula I.

The invention also provides the use of a compound or salt according to formula I for the manufacture of a medicament.

The invention also provides methods of preparing the compounds of the invention and the intermediates used in those methods.

The invention also provides methods and compositions for combination therapy of Type I and Type II diabetes. In these embodiments, the invention provides formulations and pharmaceutical compositions, as well as methods for treating Type I and Type II diabetes with the PTPase inhibitors of formula I plus additional compounds and medicaments as disclosed in more detail below. In these embodiments, the methods of the invention can comprise treatment methods for Type I and Type II diabetes where the PTPase inhibitors of formula I are formulated with a therapeutically-effective amount of said additional compounds and medicaments. In alternative embodiments, treatment methods of the invention for Type I and Type II diabetes comprise administration of the inventive PTPase inhibitors of formula I as disclosed herein concomitantly, simultaneously or together with a therapeutically-effective amount of said additional compounds and medicaments.

DETAILED DESCRIPTION OF THE INVENTION

A preferred class of compounds of formula I are compounds of formula I-a, wherein, $R_2$ is phenyl, phenyl($C_1$-$C_4$) alkyl (such as benzyl, or phenethyl), $C_1$-$C_6$ alkyl (such as methyl, ethyl, isopropyl, isopropyl, or pentyl), —($C_1$-$C_4$) alkyl-C(O)$NH_2$, —($C_1$-$C_4$) alkyl-C(O)NH($C_1$-$C_4$)alkyl, —($C_1$-$C_4$) alkyl-C(O)N($C_1$-$C_4$)alkyl($C_1$-$C_4$)alkyl, —($C_1$-$C_4$) alkyl-S(O)$_b$—($C_1$-$C_4$) alkyl, ($C_1$-$C_4$) hydroxyalkyl, —($C_1$-$C_4$) alkyl-phthalimidyl, —($C_1$-$C_4$) alkyl-piperidinyl, —($C_1$-$C_4$) alkyl-pyrrolidinyl, —($C_1$-$C_4$) alkyl-morpholinyl, wherein the phthalimidyl, piperidinyl, pyrrolidinyl, or morpholinyl groups are optionally fused to a phenyl ring and wherein said phthalimidyl, piperidinyl, pyrrolidinyl, or morpholinyl groups are, the phenyl portion, or both are optionally substituted with a total of 1, 2, 3, or 4 groups that are independently halogen, $C_1$-$C_4$ alkyl, $C_1$-$C_4$ alkoxy, —$SO_2$—($C_1$-$C_4$) alkyl ($C_1$-$C_4$)haloalkyl, or ($C_1$-$C_4$)haloalkoxy;

wherein b is 0, 1, or 2; and

Q is H, pyrido[1,2-a]indolyl, indolyl, isoindolyl, indolizinyl, imidazo[1,2-a]pyridine, -phenyl-C(O)-phenyl, -phenyl-($C_1$-$C_4$) alkyl-phenyl, -pyridyl-phenyl, fluorenyl, -fluorenyl-pyridyl, -fluorenyl-phenyl, -benzofuranyl-($C_1$-$C_4$) alkyl-phenyl, -benzimidazolyl-($C_1$-$C_4$) alkyl-phenyl, benzoxazolyl-($C_1$-$C_4$) alkyl-phenyl, indolizinyl, benzofuranyl, -indolyl-($C_1$-$C_4$)alkyl-phenyl, -phenyl-benzoxazolyl, benzo[b]thienyl, dibenzo[b,d]furan, phenyl, or dibenzothienyl, each of which is optionally substituted with 1, 2, 3, or 4 groups that are independently $C_1$-$C_6$ alkyl, $C_1$-$C_4$ alkoxycarbonyl, $C_1$-$C_6$ alkoxy, halogen, haloalkyl, haloalkoxy, $NR_6R_7$, or phenyl;

wherein
$R_6$ and $R_7$ are independently H, $C_1$-$C_6$ alkyl, aryl($C_1$-$C_6$) alkyl, alkanoyl, phenyl($C_1$-$C_4$)alkanoyl, alkoxycarbonyl, phenyl($C_1$-$C_4$)alkoxycarbonyl, pyridylcarbonyl, pyridyl, piperidinyl, pyrrolidinylcarbonyl, —C(O)$NH_2$, —C(O)NH($C_1$-$C_6$)alkyl, —C(O)N($C_1$-$C_6$)alkyl ($C_1$-$C_6$)alkyl, or —$SO_2$-phenyl, wherein the cyclic groups are optionally substituted with 1, 2, 3, or 4 groups that are independently halogen, $C_1$-$C_4$ alkyl, $C_1$-$C_4$ alkoxy, $NO_2$, OH, $NH_2$, NH($C_1$-$C_6$)alkyl, N($C_1$-$C_6$)alkyl($C_1$-$C_6$)alkyl, $CF_3$ or $OCF_3$.

Particularly preferred compounds of formula I are those where $R_1$ is H. Compounds of formula I having $R_1$ groups that are $C_1$-$C_6$ alkyl, benzyl and allyl are preferred as intermediates.

A preferred class of compounds of formula I-a are compounds of formula I-b, wherein, the A-ring is selected from phenyl, naphthyl, pyridyl, benzofuranyl, dibenzofuranyl, pyrrolyl, furanyl, isoindolyl, or indolyl each of which is optionally substituted with 1, 2, or 3 groups that are independently, halogen, $C_1$-$C_4$ alkyl, $C_1$-$C_4$ alkoxy, $C_1$-$C_4$ haloalkyl, $C_1$-$C_4$ haloalkoxy, $NO_2$, $NH_2$, NH($C_1$-$C_6$)alkyl, or N($C_1$-$C_6$)alkyl($C_1$-$C_6$) alkyl; and $R_{20}$, $R_{21}$, $R_{22}$, and $R_{23}$ are independently selected from H, phenylalkoxy, phenylalkyl, halogen, alkyl, OH, alkoxy, $NO_2$, $NH_2$, NH($C_1$-$C_6$)alkyl, N($C_1$-$C_6$)alkyl($C_1$-$C_6$)alkyl, NH-phenyl, NHC(O)—($C_1$-$C_4$) alkyl-phenyl, N($C_1$-$C_4$ alkyl)C(O)—($C_1$-$C_4$) alkyl-phenyl, N($C_1$-$C_4$)alkyl-phenyl, —$NHSO_2$-phenyl, or —N($C_1$-$C_4$alkyl)$SO_2$phenyl, wherein the phenyl groups are optionally substituted with 1, 2, 3, or 4 groups that are independently $C_1$-$C_6$ alkyl, $C_1$-$C_6$ alkoxy, halogen, OH, $NO_2$, $C_1$-$C_2$ haloalkyl, or $C_1$-$C_2$ haloalkoxy.

A preferred class of compounds of formula I-b are compounds of formula I-c, wherein, L is —$SO_2$NH—, —$SO_2$N($C_1$-$C_4$ alkyl)-, —$NHSO_2$, O, —C(O)NH—, —C(O)N($C_1$-$C_4$)alkyl-, —$SO_2$—, —C(O)—($C_1$-$C_4$) alkyl-, —($C_1$-$C_4$) alkyl-C(O)—, —NH—, —N($C_1$-$C_4$ alkyl)-, wherein the alkyl group is optionally substituted with phenyl, which is optionally substituted with 1, 2, 3, or 4 groups that are independently $C_1$-$C_6$ alkyl, $C_1$-$C_6$ alkoxy, halogen, OH, $NO_2$, $C_1$-$C_4$ haloalkyl, or $C_1$-$C_4$ haloalkoxy.

A preferred class of compounds of formula I-c are compounds of formula I-d, wherein, the A-ring is selected from naphthyl, benzofuranyl, dibenzofuranyl, isoindolyl, or indolyl each of which is optionally substituted with 1, 2, or 3 groups that are independently, halogen, $C_1$-$C_4$ alkyl, $C_1$-$C_4$ alkoxy, $C_1$-$C_4$ haloalkyl, $C_1$-$C_4$ haloalkoxy, $NO_2$, $NH_2$, NH($C_1$-$C_6$)alkyl, or N($C_1$-$C_6$)alkyl($C_1$-$C_6$) alkyl.

A preferred class of compounds of formula I-d are compounds of formula I-e, the A-ring is benzofuranyl, dibenzofuranyl, or indolyl each of which is optionally substituted with 1, 2, or 3 groups that are independently, halogen, $C_1$-$C_4$ alkyl, $C_1$-$C_4$ alkoxy, $C_1$-$C_4$ haloalkyl, $C_1$-$C_4$ haloalkoxy, $NO_2$, $NH_2$, NH($C_1$-$C_6$)alkyl, or N($C_1$-$C_6$)alkyl($C_1$-$C_6$)alkyl.

A preferred class of compounds of formula I-e are compounds of formula I-f, the A-ring is indolyl which is optionally substituted with 1, 2, or 3 groups that are independently, halogen, $C_1$-$C_4$ alkyl, $C_1$-$C_4$ alkoxy, $CF_3$, $OCF_3$, $NO_2$, $NH_2$, NH($C_1$-$C_6$) alkyl, or N($C_1$-$C_6$)alkyl($C_1$-$C_6$)alkyl.

A preferred class of compounds of formula I-c are compounds of formula I-g, the A-ring is selected from pyridyl, pyrrolyl, or furanyl, each of which is optionally substituted with 1, 2, or 3 groups that are independently, halogen, $C_1$-$C_4$ alkyl, $C_1$-$C_4$ alkoxy, $C_1$-$C_4$ haloalkyl, $C_1$-$C_4$ haloalkoxy, $NO_2$, $NH_2$, NH($C_1$-$C_6$)alkyl, or N($C_1$-$C_6$)alkyl($C_1$-$C_6$)alkyl.

A preferred class of compounds of formulas I-d, I-e, I-f, or I-g, are compounds of formula I-h, wherein $L_3$ is a bond, absent, —($C_1$-$C_4$)alkyl-O—, —O—($C_1$-$C_4$) alkyl, —($C_1$-$C_4$) alkyl-, or —C(O)—; and Q is H, pyrido[1,2-a]indolyl, indolyl, imidazo[1,2-a]pyridine, -phenyl-C(O)-phenyl, -phenyl-($C_1$-$C_4$)alkyl-phenyl, fluorenyl, -benzofuranyl-($C_1$-$C_4$)alkyl-phenyl, indolizinyl, benzofuranyl, -indolyl-($C_1$-$C_4$)alkyl-phenyl, -phenyl-benzoxazolyl, benzo[b]thienyl, dibenzo[b,d]furan, phenyl, or dibenzothienyl, each of which is optionally substituted with 1, 2, 3, or 4 groups that are independently $C_1$-$C_6$ alkyl, $C_1$-$C_4$ alkoxycarbonyl, $C_1$-$C_6$ alkoxy, halogen, haloalkyl, haloalkoxy, $NR_6R_7$, or phenyl.

A preferred class of compounds of formula I-h are compounds of formula I-i, $L_3$ is a bond, —O—($C_1$-$C_4$)alkyl-, or —($C_1$-$C_4$) alkyl; and Q is H, pyrido[1,2-a]indolyl, indolyl, -phenyl-C(O)-phenyl, -benzofuranyl-($C_1$-$C_4$) alkyl-phenyl, indolizinyl, or benzofuranyl, each of which is optionally substituted with 1, 2, 3, or 4 groups that are independently $C_1$-$C_6$ alkyl, $C_1$-$C_4$ alkoxycarbonyl, $C_1$-$C_6$ alkoxy, halogen, haloalkyl, haloalkoxy, $NR_6R_7$, or phenyl.

A preferred class of compounds of formula I-i are compounds of formula I-j, $R_2$ is phenyl, phenyl($C_1$-$C_4$) alkyl(such as benzyl or phenethyl), $C_1$-$C_6$ alkyl (methyl, ethyl, isopropyl, isopropyl, isobutyl, or pentyl), —($C_1$-$C_4$) alkyl-C(O)$NH_2$, —($C_1$-$C_4$) alkyl-S(O)$_b$—($C_1$-$C_4$) alkyl, ($C_1$-$C_4$) hydroxyalkyl, wherein the phenyl groups are optionally substituted with 1, 2, 3, or 4 groups that are independently halogen, $C_1$-$C_4$ alkyl, $C_1$-$C_4$ alkoxy, —$SO_2$—($C_1$-$C_4$) alkyl, $CF_3$ or $OCF_3$.

A preferred class of compounds of formula I-j are compounds of formula I-k, wherein $R_1$ is H, or $C_1$-$C_6$ alkyl; and $R_{20}$, $R_{21}$, $R_{22}$, and $R_{23}$ are independently selected from H, halogen, alkyl, OH, alkoxy, $NO_2$, $NH_2$, NH($C_1$-$C_6$)alkyl, N($C_1$-$C_6$alkyl) ($C_1$-$C_6$alkyl), NH-phenyl, or NHC(O)—($C_1$-$C_4$) alkyl-phenyl, wherein the phenyl group is optionally substituted with 1, 2, 3, or 4 groups that are independently $C_1$-$C_6$ alkyl, $C_1$-$C_6$ alkoxy, halogen, OH, $NO_2$, $CF_3$, or $OCF_3$.

A preferred class of compounds of formula I-k are compounds of formula I-1, wherein n is 0 or 1;

$R_1$ is H;

$R_{22}$ and $R_{23}$ are both hydrogen; and $R_{20}$, and $R_{21}$, are independently selected from H, halogen, alkyl, OH, alkoxy, $NO_2$, $NH_2$, NH($C_1$-$C_6$)alkyl, or N($C_1$-$C_6$alkyl) ($C_1$-$C_6$alkyl).

A preferred class of compounds of formula I-1 are compounds of formula I-m, wherein $R_6$ is hydrogen; and $R_7$ is H, $C_1$-$C_6$ alkyl, benzyl, phenethyl, $C_2$-$C_6$ alkanoyl, phenyl($C_1$-$C_4$)alkanoyl, $C_1$-$C_4$alkoxycarbonyl, phenyl ($C_1$-$C_4$) alkoxycarbonyl, pyridylcarbonyl, pyridyl, piperidinyl, pyrrolidinylcarbonyl, or —$SO_2$-phenyl, wherein the cyclic groups are optionally substituted with 1, 2, 3, or 4 groups that are independently halogen, $C_1$-$C_4$ alkyl, $C_1$-$C_4$ alkoxy, $NO_2$, OH, $NH_2$, NH($C_1$-$C_6$)alkyl, N($C_1$-$C_6$)alkyl($C_1$-$C_6$)alkyl, $CF_3$ or $OCF_3$.

A preferred class of compounds of formula I-m are compounds of formula I-n, wherein $R_2$ is phenyl, phenyl($C_1$-$C_4$) alkyl(such as benzyl, phenethyl), or $C_1$-$C_6$ alkyl (such as methyl, ethyl, propyl, isopropyl, isobutyl, or pentyl), wherein the phenyl groups are optionally substituted with 1, 2, 3, or 4 groups that are independently halogen, $C_1$-$C_4$ alkyl, $C_1$-$C_4$ alkoxy, —$SO_2$—($C_1$-$C_4$) alkyl, $CF_3$ or $OCF_3$.

A preferred class of compounds of formula I-n are compounds of formula I-o, wherein $R_2$ is phenyl, wherein the phenyl group is optionally substituted with 1, 2, 3, or 4 groups that are independently halogen, $C_1$-$C_4$ alkyl, $C_1$-$C_4$ alkoxy, —$SO_2$—($C_1$-$C_4$) alkyl, $CF_3$ or $OCF_3$.

A preferred class of compounds of formula I-o are compounds of formula I-p, wherein $R_2$ is phenyl($C_1$-$C_4$) alkyl(such as benzyl or phenethyl), wherein the phenyl groups are optionally substituted with 1, 2, 3, or 4 groups that are independently halogen, $C_1$-$C_4$ alkyl, $C_1$-$C_4$ alkoxy, —$SO_2$—($C_1$-$C_4$) alkyl, $CF_3$ or $OCF_3$.

In another aspect, the phenyl($C_1$-$C_4$) alkyl is benzyl or phenethyl.

A preferred class of compounds of formula I-n are compounds of formula I-q, wherein $R_2$ is $C_1$-$C_6$ alkyl (such as methyl, ethyl, isopropyl, isobutyl or pentyl).

In another aspect, the $C_1$-$C_6$ alkyl is methyl, ethyl, isopropyl, or isobutyl.

A preferred class of compounds of formula I-m are compounds of formula I-r, wherein $R_2$ is —($C_1$-$C_4$) alkyl-C(O)$NH_2$, —($C_1$-$C_4$) alkyl-S(O)$_b$—($C_1$-$C_4$) alkyl, or ($C_1$-$C_4$) hydroxyalkyl, wherein b is 0, 1 or 2.

A Preferred class of compounds of formula I-c include compounds of formula II:

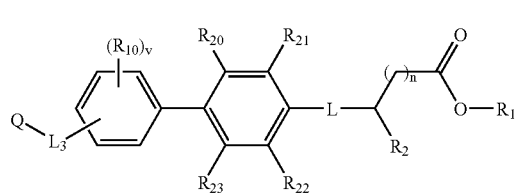

(II)

wherein
$R_1$ is H or $C_1$-$C_6$ alkyl (preferably $R_1$ is H);
$R_2$ is phenyl, phenyl($C_1$-$C_4$) alkyl(such as benzyl, phenethyl), $C_1$-$C_6$ alkyl (such as methyl, ethyl, isopropyl, isobutyl, pentyl), —($C_1$-$C_4$) alkyl-C(O)NH$_2$, —($C_1$-$C_4$) alkyl-S(O)$_b$—($C_1$-$C_4$) alkyl, or ($C_1$-$C_4$) hydroxyalkyl, wherein the phenyl groups are optionally substituted with 1, 2, 3, or 4 groups that are independently halogen, $C_1$-$C_4$ alkyl, $C_1$-$C_4$ alkoxy, —SO$_2$—($C_1$-$C_4$) alkyl, ($C_1$-$C_4$)haloalkyl (such as CF$_3$), or ($C_1$-$C_4$) haloalkoxy (such as OCF$_3$);
v is 0, 1, 2, 3, or 4;
$R_{10}$ at each occurrence is independently halogen, $C_1$-$C_4$ alkyl, $C_1$-$C_4$ alkoxy, $C_1$-$C_4$ haloalkyl, $C_1$-$C_4$ haloalkoxy, NO$_2$, NH$_2$, NH($C_1$-$C_6$)alkyl, or N($C_1$-$C_6$)alkyl($C_1$-$C_6$) alkyl; and
$L_3$ is a bond, absent, —O—($C_1$-$C_4$)alkyl, —($C_1$-$C_4$) alkyl-, or —C(O)—.

A Preferred class of compounds of formula II include compounds of formula II-a, wherein
Q is H, pyrido[1,2-a]indolyl, indolyl, imidazo[1,2-a]pyridine, -phenyl-C(O)-phenyl, -phenyl-($C_1$-$C_4$) alkyl-phenyl, fluorenyl, -benzofuranyl-($C_1$-$C_4$) alkyl-phenyl, indolizinyl, benzofuranyl, -indolyl-($C_1$-$C_4$)alkyl-phenyl, -phenyl-benzoxazolyl, benzo[b]thienyl, dibenzo[b,d]furan, phenyl, or dibenzothienyl, each of which is optionally substituted with 1, 2, 3, or 4 groups that are independently $C_1$-$C_6$ alkyl, $C_1$-$C_4$ alkoxycarbonyl, $C_1$-$C_6$ alkoxy, halogen, haloalkyl, haloalkoxy, NR$_6$R$_7$, or phenyl; wherein
$R_6$ and $R_7$ are independently H, $C_1$-$C_6$ alkyl, aryl($C_1$-$C_6$) alkyl, alkanoyl, phenyl ($C_0$-$C_4$)alkanoyl, alkoxycarbonyl, phenyl ($C_1$-$C_4$) alkoxycarbonyl, pyridylcarbonyl, pyridyl, pyrrolidinylcarbonyl, or —SO$_2$-phenyl, wherein the cyclic groups are optionally substituted with 1, 2, 3, or 4 groups that are independently halogen, $C_1$-$C_4$ alkyl, $C_1$-$C_4$ alkoxy, NO$_2$, OH, NH$_2$, NH($C_1$-$C_6$) alkyl, N($C_1$-$C_6$)alkyl($C_1$-$C_6$)alkyl, CF$_3$ or OCF$_3$.

A Preferred class of compounds of formula II-a include compounds of formula II-b, wherein
$R_2$ is phenyl, phenyl($C_1$-$C_4$) alkyl (such as benzyl or phenethyl), or ($C_1$-$C_6$)alkyl, wherein the phenyl groups are optionally substituted with 1, 2, 3, or 4 groups that are independently halogen, $C_1$-$C_4$ alkyl, $C_1$-$C_4$ alkoxy, or —SO$_2$—($C_1$-$C_4$) alkyl, CF$_3$ or OCF$_3$; and
$R_{20}$, $R_{21}$, $R_{22}$, and $R_{23}$ are independently selected from H, halogen, alkyl, OH, alkoxy, NO$_2$, NH$_2$, NH($C_1$-$C_6$)alkyl, or N($C_1$-$C_6$alkyl) ($C_1$-$C_6$alkyl).

A Preferred class of compounds of formula II-b include compounds of formula II-c, wherein
$R_{22}$ and $R_{23}$ are both hydrogen.

A Preferred class of compounds of formula II-c include compounds of formula II-d, wherein
$R_1$ and $R_6$ are hydrogen; and
v is 0 or 1.

A Preferred class of compounds of formula II-b include compounds of formula II-e, wherein
$L_3$ is a bond, —O—($C_1$-$C_4$)alkyl, —($C_1$-$C_4$) alkyl-, or —C(O)—;
Q is indolyl, -phenyl-C(O)-phenyl, -benzofuranyl-($C_1$-$C_4$) alkyl-phenyl, indolizinyl, benzofuranyl, -indolyl-($C_1$-$C_4$) alkyl-phenyl, benzo[b]thienyl, dibenzo[b,d]furan, phenyl, or dibenzothienyl, each of which is optionally substituted with 1, 2, 3, or 4 groups that are independently $C_1$-$C_6$ alkyl, $C_1$-$C_4$ alkoxycarbonyl, $C_1$-$C_6$ alkoxy, halogen, haloalkyl, haloalkoxy, NR$_6$R$_7$, or phenyl; wherein
$R_6$ and $R_7$ are independently H, $C_1$-$C_6$ alkyl, phenyl($C_1$-$C_6$)alkyl, alkanoyl, phenyl($C_1$-$C_4$)alkanoyl, alkoxycarbonyl, pyridylcarbonyl, pyridyl, pyrrolidinylcarbonyl, or —SO$_2$-phenyl, wherein the cyclic groups are optionally substituted with 1, 2, 3, or 4 groups that are independently halogen, $C_1$-$C_4$ alkyl, $C_1$-$C_4$ alkoxy, NO$_2$, OH, NH$_2$, NH($C_1$-$C_6$)alkyl, N($C_1$-$C_6$)alkyl($C_1$-$C_6$)alkyl, CF$_3$ or OCF$_3$.

A Preferred class of compounds of formula II-e include compounds of formula III

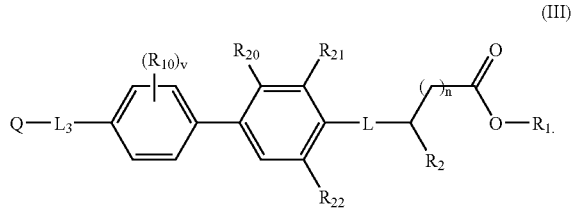

(III)

A Preferred class of compounds of formula III include compounds of formula III-a, wherein
L is —SO$_2$NH—, —SO$_2$N($C_1$-$C_4$ alkyl)-, or —SO$_2$— wherein the alkyl group is optionally substituted with phenyl, which is optionally substituted with 1, 2, 3, or 4 groups that are independently $C_1$-$C_6$ alkyl, $C_1$-$C_6$ alkoxy, halogen, OH, NO$_2$, $C_1$-$C_4$ haloalkyl, or $C_1$-$C_4$ haloalkoxy.

A Preferred class of compounds of formula III-a include compounds of formula III-b, wherein
$R_1$ is H;
$R_{21}$ is H, NO$_2$, $C_1$-$C_6$ alkyl, or halogen; and
$R_2$ is phenyl, benzyl, or ($C_1$-$C_6$)alkyl, wherein each phenyl group is optionally substituted with 1, 2, 3, or 4 groups that are independently halogen, $C_1$-$C_4$ alkyl, $C_1$-$C_4$ alkoxy, or —SO$_2$—($C_1$-$C_4$) alkyl, CF$_3$ or OCF$_3$.

A Preferred class of compounds of formula III-b include compounds of formula III-c, wherein
L is —SO$_2$NH—, or —SO$_2$N($C_1$-$C_4$ alkyl)-wherein the alkyl group is optionally substituted with phenyl, which is optionally substituted with 1, 2, 3, or 4 groups that are independently $C_1$-$C_6$ alkyl, $C_1$-$C_6$ alkoxy, halogen, OH, NO$_2$, $C_1$-$C_4$ haloalkyl, or $C_1$-$C_4$ haloalkoxy.

A Preferred class of compounds of formula III-c include compounds of formula III-d, wherein
L is —SO$_2$N($C_1$-$C_4$ alkyl)-.

A Preferred class of compounds of formula III-c include compounds of formula III-e, wherein
L is —SO$_2$N($C_1$-$C_4$ alkyl)-wherein the alkyl group is substituted with phenyl, which is optionally substituted with 1, 2, 3, or 4 groups that are independently $C_1$-$C_6$ alkyl, $C_1$-$C_6$ alkoxy, halogen, OH, NO$_2$, CF$_3$ or OCF$_3$.

A Preferred class of compounds of formula III-c include compounds of formula III-f, wherein
L is —SO$_2$NH—.

A Preferred class of compounds according to any one of formulas III-b, III-c, III-d, or III-e, include compounds of formula III-g, wherein $R_2$ is phenyl or benzyl, each of which is substituted at position number 3 or 4 of the $R_2$ phenyl ring with a halogen, $CF_3$ or $OCF_3$.

A Preferred class of compounds according to any one of formulas III-b, III-c, III-d, or III-e, include compounds of formula III-h, wherein $R_2$ is $C_1$-$C_6$ alkyl.

A Preferred class of compounds of formula III-b include compounds of formula III-i, wherein $L_3$ is a bond, —O—($C_1$-$C_4$)alkyl, or —($C_1$-$C_4$) alkyl-;

Q is-benzofuranyl-($C_1$-$C_4$) alkyl-phenyl, indolizinyl, benzofuranyl, dibenzo[b,d]furan, or dibenzothienyl, each of which is optionally substituted with 1, 2, 3, or 4 groups that are independently $C_1$-$C_6$ alkyl, $C_1$-$C_4$ alkoxycarbonyl, $C_1$-$C_6$ alkoxy, halogen, haloalkyl, haloalkoxy, $NR_6R_7$, or phenyl;

wherein
$R_6$ and $R_7$ are independently H, $C_1$-$C_6$ alkyl, phenyl($C_1$-$C_6$)alkyl, alkanoyl, phenyl($C_1$-$C_4$)alkanoyl, alkoxycarbonyl, pyridylcarbonyl, pyridyl, pyrrolidinylcarbonyl, or —$SO_2$-phenyl, wherein the cyclic groups are optionally substituted with 1, 2, 3, or 4 groups that are independently halogen, $C_1$-$C_4$ alkyl, $C_1$-$C_4$ alkoxy, $NO_2$, OH, $NH_2$, $NH(C_1$-$C_6)$alkyl, $N(C_1$-$C_6)$alkyl($C_1$-$C_6)$alkyl, $CF_3$ or $OCF_3$.

A Preferred class of compounds of formula III-i include compounds of formula III-j, wherein Q is-benzofuranyl-($C_1$-$C_4$) alkyl-phenyl, indolizinyl, benzofuranyl, dibenzo[b,d]furan, or dibenzothienyl, each of which is optionally substituted with 1, 2, 3, or 4 groups that are independently $C_1$-$C_6$ alkyl, $C_1$-$C_4$ alkoxycarbonyl, $C_1$-$C_6$ alkoxy, halogen, haloalkyl, or haloalkoxy.

A Preferred class of compounds of formula III include compounds of formula III-k, wherein L is —O—.

A Preferred class of compounds of formula III-k include compounds of formula III-l, wherein $R_1$ is H;
$R_{21}$ is H, $NO_2$, $C_1$-$C_6$ alkyl, or halogen; and
$R_2$ is phenyl, phenyl($C_1$-$C_4$)alkyl, or ($C_1$-$C_6$)alkyl, wherein each phenyl group is optionally substituted with 1, 2, 3, or 4 groups that are independently halogen, $C_1$-$C_4$ alkyl, $C_1$-$C_4$ alkoxy, or —$SO_2$—($C_1$-$C_4$) alkyl, $CF_3$ or $OCF_3$.

A Preferred class of compounds of formula III-l include compounds of formula III-m, wherein $R_2$ is phenyl or benzyl, wherein each is optionally substituted with 1, 2, 3, or 4 groups that are independently halogen, $C_1$-$C_4$ alkyl, $C_1$-$C_4$ alkoxy, —$SO_2$—($C_1$-$C_4$) alkyl, $CF_3$ or $OCF_3$.

A Preferred class of compounds of formula III-m include compounds of formula III-n, wherein $R_2$ is phenyl or benzyl, each of which is substituted at position number 3 or 4 of the $R_2$ phenyl ring with a halogen, $CF_3$ or $OCF_3$.

A Preferred class of compounds of formula III-l include compounds of formula III-O, wherein $R_2$ is phenyl which is substituted at position number 3 or 4 of the $R_2$ phenyl ring with a halogen, $CF_3$ or $OCF_3$.

A Preferred class of compounds of formula III-l include compounds of formula III-p, wherein $R_2$ is benzyl, which is substituted at position number 3 or 4 of the $R_2$ phenyl ring with a halogen, $CF_3$ or $OCF_3$.

A Preferred class of compounds of formula III-l include compounds of formula III-q, wherein $R_2$ is $C_1$-$C_6$ alkyl.

A Preferred class of compounds of formula III-l include compounds of formula III-r, wherein $L_3$ is a bond, —O—($C_1$-$C_4$)alkyl, or —($C_1$-$C_4$) alkyl-;

Q is indolyl, -phenyl-C(O)-phenyl, -benzofuranyl-($C_1$-$C_4$) alkyl-phenyl, indolizinyl, benzofuranyl, or-indolyl-($C_1$-$C_4$)alkyl-phenyl, each of which is optionally substituted with 1, 2, 3, or 4 groups that are independently $C_1$-$C_6$ alkyl, $C_1$-$C_4$ alkoxycarbonyl, $C_1$-$C_6$ alkoxy, halogen, haloalkyl, haloalkoxy, $NR_6R_7$, or phenyl; wherein $R_6$ and $R_7$ are independently H, $C_1$-$C_6$ alkyl, phenyl($C_1$-$C_6$)alkyl, alkanoyl, phenyl($C_1$-$C_4$)alkanoyl, alkoxycarbonyl, pyridylcarbonyl, pyrrolidinylcarbonyl, or —$SO_2$-phenyl, wherein the cyclic groups are optionally substituted with 1, 2, 3, or 4 groups that are independently halogen, $C_1$-$C_4$ alkyl, $C_1$-$C_4$ alkoxy, $NO_2$, OH, $NH_2$, $NH(C_1$-$C_6)$ alkyl, $N(C_1$-$C_6)$ alkyl($C_1$-$C_6)$alkyl, $CF_3$ or $OCF_3$.

A Preferred class of compounds of formula III-r include compounds of formula III-s, wherein Q is indolyl, -phenyl-C(O)-phenyl, -benzofuranyl-($C_1$-$C_4$) alkyl-phenyl, indolizinyl, benzofuranyl, or-indolyl-($C_1$-$C_4$)alkyl-phenyl.

A Preferred class of compounds of formula III include compounds of formula III-t, wherein L is —C(O)NH—, —C(O)N($C_1$-$C_4$)alkyl-, —C(O)—($C_1$-$C_4$) alkyl-, —NH—, or —N($C_1$-$C_4$) alkyl-, wherein the alkyl groups are optionally substituted with phenyl, which is optionally substituted with 1, 2, 3, or 4 groups that are independently $C_1$-$C_6$ alkyl, $C_1$-$C_6$ alkoxy, halogen, OH, $NO_2$, $C_1$-$C_2$ haloalkyl, or $C_1$-$C_2$ haloalkoxy.

A Preferred class of compounds of formula III-l include compounds of formula III-u, wherein L is —C(O)NH—, or —C(O)N($C_1$-$C_4$)alkyl-;
$R_1$ is H;
$R_{21}$ is H, $NO_2$, $C_1$-$C_6$ alkyl, or halogen.

A Preferred class of compounds of formula III-u include compounds of formula III-v, wherein $R_2$ is phenyl, phenyl($C_1$-$C_4$)alkyl, or ($C_1$-$C_6$)alkyl, wherein each phenyl group is optionally substituted with 1, 2, 3, or 4 groups that are independently halogen, $C_1$-$C_4$ alkyl, $C_1$-$C_4$ alkoxy, or —$SO_2$—($C_1$-$C_4$) alkyl, $CF_3$ or $OCF_3$.

A Preferred class of compounds of formula III-v include compounds of formula III-w, wherein $R_2$ is phenyl or benzyl, wherein each is optionally substituted with 1, 2, 3, or 4 groups that are independently halogen, $C_1$-$C_4$ alkyl, $C_1$-$C_4$ alkoxy, —$SO_2$—($C_1$-$C_4$) alkyl, $CF_3$ or $OCF_3$.

A Preferred class of compounds of formula III-m include compounds of formula III-x, wherein $R_2$ is phenyl or benzyl, each of which is substituted at position number 3 or 4 of the $R_2$ phenyl ring with a halogen, $CF_3$ or $OCF_3$.

A Preferred class of compounds of formula III-l include compounds of formula III-y, wherein $R_2$ is phenyl which is substituted at position number 3 or 4 of the $R_2$ phenyl ring with a halogen, $CF_3$ or $OCF_3$.

A Preferred class of compounds of formula III-l include compounds of formula III-z, wherein $R_2$ is benzyl, each of which is substituted at position number 3 or 4 of the $R_2$ phenyl ring with a halogen, $CF_3$ or $OCF_3$.

A Preferred class of compounds of formula III-l include compounds of formula III-aa, wherein $R_2$ is $C_1$-$C_6$ alkyl.

A Preferred class of compounds of formula III-v include compounds of formula III-bb, wherein $L_3$ is a bond, —O—$(C_1$-$C_4)$alkyl, or —$(C_1$-$C_4)$ alkyl-;

Q is indolyl, -phenyl-C(O)-phenyl, -benzofuranyl-$(C_1$-$C_4)$ alkyl-phenyl, indolizinyl, benzofuranyl, or-indolyl-$(C_1$-$C_4)$alkyl-phenyl, each of which is optionally substituted with 1, 2, 3, or 4 groups that are independently $C_1$-$C_6$ alkyl, $C_1$-$C_4$ alkoxycarbonyl, $C_1$-$C_6$ alkoxy, halogen, haloalkyl, haloalkoxy, $NR_6R_7$, or phenyl; wherein $R_6$ and $R_7$ are independently H, $C_1$-$C_6$ alkyl, phenyl($C_1$-$C_6$)alkyl, alkanoyl, phenyl($C_1$-$C_4$)alkanoyl, alkoxycarbonyl, pyridylcarbonyl, pyrrolidinylcarbonyl, or —$SO_2$-phenyl, wherein the cyclic groups are optionally substituted with 1, 2, 3, or 4 groups that are independently halogen, $C_1$-$C_4$ alkyl, $C_1$-$C_4$ alkoxy, $NO_2$, OH, $NH_2$, NH($C_1$-$C_6$)alkyl, N($C_1$-$C_6$)alkyl($C_1$-$C_6$)alkyl, $CF_3$ or $OCF_3$.

A Preferred class of compounds of formula III-bb include compounds of formula III-cc, wherein $L_3$ is a bond, or —$(C_1$-$C_4)$ alkyl; and Q is indolyl, -phenyl-C(O)-phenyl, -benzofuranyl-$(C_1$-$C_4)$ alkyl-phenyl, indolizinyl, or benzofuranyl, each of which is optionally substituted with 1, 2, 3, or 4 groups that are independently $C_1$-$C_6$ alkyl, $C_1$-$C_4$ alkoxycarbonyl, $C_1$-$C_6$ alkoxy, halogen, haloalkyl, haloalkoxy, $NR_6R_7$, or phenyl.

A Preferred class of compounds of formula III-cc include compounds of formula III-dd, wherein Q is-benzofuranyl-$(C_1$-$C_4)$ alkyl-phenyl, indolizinyl, or benzofuranyl.

A Preferred class of compounds of formula II include compounds of formula II-f, wherein L is —NH—, or —N($C_1$-$C_4$) alkyl-.

A Preferred class of compounds of formula II-f include compounds of formula II-g, wherein $R_1$ is H;

$R_{21}$ is H, $NO_2$, $C_1$-$C_6$ alkyl, or halogen; and $R_2$ is phenyl, phenyl($C_1$-$C_4$) alkyl(such as benzyl or phenethyl), $C_1$-$C_6$ alkyl (such as methyl, ethyl, isopropyl), —$(C_1$-$C_4)$ alkyl-C(O)$NH_2$, —$(C_1$-$C_4)$ alkyl-S(O)$_b$—$(C_1$-$C_4)$ alkyl, or $(C_1$-$C_4)$ hydroxyalkyl, wherein the phenyl groups are optionally substituted with 1, 2, 3, or 4 groups that are independently halogen, $C_1$-$C_4$ alkyl, $C_1$-$C_4$ alkoxy, —$SO_2$—$(C_1$-$C_4)$ alkyl, $CF_3$ or $OCF_3$.

A Preferred class of compounds of formula II-g include compounds of formula II-h, wherein $L_3$ is a bond, —O—$(C_1$-$C_4)$alkyl, or —$(C_1$-$C_4)$ alkyl-;

Q is indolyl, -phenyl-C(O)-phenyl, -benzofuranyl-$(C_1$-$C_4)$ alkyl-phenyl, indolizinyl, benzofuranyl, or-indolyl-$(C_1$-$C_4)$alkyl-phenyl, each of which is optionally substituted with 1, 2, 3, or 4 groups that are independently $C_1$-$C_6$ alkyl, $C_1$-$C_4$ alkoxycarbonyl, $C_1$-$C_6$ alkoxy, halogen, haloalkyl, haloalkoxy, $NR_6R_7$, or phenyl; wherein $R_6$ and $R_7$ are independently H, $C_1$-$C_6$ alkyl, phenyl($C_1$-$C_6$)alkyl, alkanoyl, phenyl($C_1$-$C_4$)alkanoyl, alkoxycarbonyl, pyridylcarbonyl, pyrrolidinylcarbonyl, or —$SO_2$-phenyl, wherein the cyclic groups are optionally substituted with 1, 2, 3, or 4 groups that are independently halogen, $C_1$-$C_4$ alkyl, $C_1$-$C_4$ alkoxy, $NO_2$, OH, $NH_2$, NH($C_1$-$C_6$)alkyl, N($C_1$-$C_6$)alkyl($C_1$-$C_6$)alkyl, $CF_3$ or $OCF_3$.

A Preferred class of compounds of formula II-h include compounds of formula II-i, wherein $L_3$ is a bond, or —$(C_1$-$C_4)$ alkyl; and Q is indolyl, -benzofuranyl-$(C_1$-$C_4)$ alkyl-phenyl, indolizinyl, benzofuranyl, or-indolyl-$(C_1$-$C_4)$alkyl-phenyl, each of which is optionally substituted with 1, 2, 3, or 4 groups that are independently $C_1$-$C_6$ alkyl, $C_1$-$C_4$ alkoxycarbonyl, $C_1$-$C_6$ alkoxy, halogen, $CF_3$ or $OCF_3$.

A Preferred class of compounds of formula II-i include compounds of formula II-j, wherein $R_2$ is —$(C_1$-$C_4)$ alkyl-C(O)$NH_2$, —$(C_1$-$C_4)$ alkyl-S(O)$_b$—$(C_1$-$C_4)$ alkyl, or $(C_1$-$C_4)$ hydroxyalkyl.

A Preferred class of compounds of formula II-i include compounds of formula II-k, wherein $R_2$ is —$(C_1$-$C_4)$ alkyl-C(O)$NH_2$.

A Preferred class of compounds of formula II-i include compounds of formula II-l, wherein $R_2$ is —$(C_1$-$C_4)$ alkyl-S(O)$_b$—$(C_1$-$C_4)$ alkyl.

A Preferred class of compounds of formula II-i include compounds of formula II-m, wherein $R_2$ is $(C_1$-$C_4)$ hydroxyalkyl.

A Preferred class of compounds of formulas II-h, II-i, II-j, II-k, II-l, or II-m include compounds of formula II-n, wherein $R_2$ is phenyl, phenyl($C_1$-$C_4$)alkyl, or $(C_1$-$C_6$)alkyl, wherein each phenyl group is optionally substituted with 1, 2, 3, or 4 groups that are independently halogen, $C_1$-$C_4$ alkyl, $C_1$-$C_4$ alkoxy, or —$SO_2$—$(C_1$-$C_4)$ alkyl, $CF_3$ or $OCF_3$.

A Preferred class of compounds of formula II-n include compounds of formula II-o, wherein $R_2$ is phenyl or benzyl, wherein each is optionally substituted with 1, 2, 3, or 4 groups that are independently halogen, $C_1$-$C_4$ alkyl, $C_1$-$C_4$ alkoxy, —$SO_2$—$(C_1$-$C_4)$ alkyl, $CF_3$ or $OCF_3$.

A Preferred class of compounds of formula II-o include compounds of formula II-p, wherein $R_2$ is phenyl or benzyl, each of which is substituted at position number 3 or 4 of the $R_2$ phenyl ring with a halogen, $CF_3$ or $OCF_3$.

A Preferred class of compounds of formula II-p include compounds of formula II-q, wherein $R_2$ is phenyl which is substituted at position number 3 or 4 of the $R_2$ phenyl ring with a halogen, $CF_3$ or $OCF_3$.

Another Preferred class of compounds of formula II-o include compounds of formula II-r, wherein $R_2$ is benzyl, which is substituted at position number 3 or 4 of the $R_2$ phenyl ring with a halogen, $CF_3$ or $OCF_3$.

A Preferred class of compounds of formula II-n include compounds of formula II-s, wherein $R_2$ is $C_1$-$C_6$ alkyl.

Another preferred class of compounds of formula I-a include compounds of formula IV, wherein

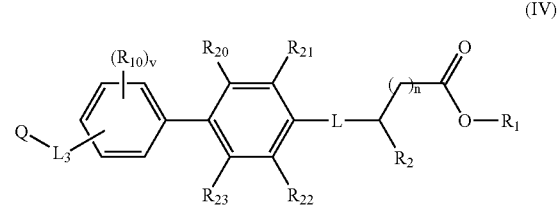

(IV)

wherein v is 0, 1, 2, 3, or 4;

$R_{10}$ at each occurrence is independently halogen, $C_1$-$C_4$ alkyl, $C_1$-$C_4$ alkoxy, $C_1$-$C_4$ haloalkyl, $C_1$-$C_4$ haloalkoxy, $NO_2$, $NH_2$, NH($C_1$-$C_6$)alkyl, or N($C_1$-$C_6$)alkyl($C_1$-$C_6$) alkyl; and L is —C(O)—$(C_1$-$C_4)$ alkyl-, —$(C_1$-$C_4)$ alkyl-C(O)—, wherein the alkyl groups are optionally substituted with phenyl, which is optionally substituted with 1, 2, 3, or 4 groups that are independently $C_1$-$C_6$ alkyl, $C_1$-$C_6$ alkoxy, halogen, OH, $NO_2$, $C_1$-$C_4$ haloalkyl, or $C_1$-$C_4$ haloalkoxy.

A Preferred class of compounds of formula IV include compounds of formula IV-a, wherein $R_1$ is H;

$R_{20}$, $R_{22}$, and $R_{23}$ are independently selected from H, halogen, alkyl, OH, alkoxy, $NO_2$, $NH_2$, $NH(C_1-C_6)$alkyl, or $N(C_1-C_6$alkyl) $(C_1-C_6$alkyl);

$R_{21}$ is H, $NO_2$, $C_1-C_6$ alkyl, or halogen; and $R_2$ is phenyl, phenyl$(C_1-C_4)$ alkyl(such as benzyl or phenethyl), $C_1-C_6$ alkyl (such as methyl, ethyl, isopropyl, isobutyl), —$(C_1-C_4)$ alkyl-phthalimidyl, —$(C_1-C_4)$ alkyl-piperidinyl, —$(C_1-C_4)$ alkyl-pyrrolidinyl, —$(C_1-C_4)$ alkyl-morpholinyl, wherein the phthalimidyl, piperidinyl, pyrrolidinyl, or morpholinyl groups are optionally fused to a phenyl ring and wherein said phthalimidyl, piperidinyl, pyrrolidinyl, or morpholinyl groups are, the phenyl portion, or both are optionally substituted with a total of 1, 2, 3, or 4 groups that are independently halogen, $C_1-C_4$ alkyl, $C_1-C_4$ alkoxy, —$SO_2$—$(C_1-C_4)$ alkyl $(C_1-C_4)$haloalkyl, or $(C_1-C_4)$haloalkoxy;

wherein b is 0, 1, or 2.

A Preferred class of compounds of formula IV-a include compounds of formula IV-b, wherein $L_3$ is a bond, —O—$(C_1-C_4)$alkyl, or —$(C_1-C_4)$ alkyl-;

Q is indolyl, -phenyl-C(O)-phenyl, -benzofuranyl-$(C_1-C_4)$ alkyl-phenyl, indolizinyl, benzofuranyl, -indolyl-$(C_1-C_4)$ alkyl-phenyl, dibenzo[b,d]furan, or dibenzothienyl, each of which is optionally substituted with 1, 2, 3, or 4 groups that are independently $C_1-C_6$ alkyl, $C_1-C_4$ alkoxycarbonyl, $C_1-C_6$ alkoxy, halogen, haloalkyl, haloalkoxy, $NR_6R_7$, or phenyl;

wherein $R_6$ and $R_7$ are independently H, $C_1-C_6$ alkyl, phenyl$(C_1-C_6)$alkyl, alkanoyl, phenyl$(C_1-C_4)$alkanoyl, alkoxycarbonyl, pyridylcarbonyl, pyrrolidinylcarbonyl, or —$SO_2$-phenyl, wherein the cyclic groups are optionally substituted with 1, 2, 3, or 4 groups that are independently halogen, $C_1-C_4$ alkyl, $C_1-C_4$ alkoxy, $NO_2$, OH, $NH_2$, $NH(C_1-C_6)$alkyl, $N(C_1-C_6)$alkyl$(C_1-C_6)$alkyl, $CF_3$ or $OCF_3$.

A Preferred class of compounds of formula IV-b include compounds of formula IV-c, wherein $R_2$ is —$(C_1-C_4)$ alkyl-phthalimidyl, —$(C_1-C_4)$ alkyl-piperidinyl, —$(C_1-C_4)$ alkyl-pyrrolidinyl, —$(C_1-C_4)$ alkyl-morpholinyl, wherein the phthalimidyl, piperidinyl, pyrrolidinyl, or morpholinyl groups are optionally fused to a phenyl ring and wherein said phthalimidyl, piperidinyl, pyrrolidinyl, or morpholinyl groups are, the phenyl portion, or both are optionally substituted with a total of 1, 2, 3, or 4 groups that are independently halogen, $C_1-C_4$ alkyl, $C_1-C_4$ alkoxy, —$SO_2$—$(C_1-C_4)$ alkyl $(C_1-C_4)$haloalkyl, or $(C_1-C_4)$haloalkoxy.

A Preferred class of compounds of formula IV-c include compounds of formula IV-d, wherein $R_2$ is —$(C_1-C_4)$ alkyl-phthalimidyl, —$(C_1-C_4)$ alkyl-piperidinyl, or —$(C_1-C_4)$ alkyl-pyrrolidinyl, wherein the phthalimidyl, piperidinyl, pyrrolidinyl, or morpholinyl groups are optionally fused to a phenyl ring and wherein said phthalimidyl, piperidinyl, or pyrrolidinyl, groups are, the phenyl portion, or both are optionally substituted with a total of 1, 2, 3, or 4 groups that are independently halogen, $C_1-C_4$ alkyl, $C_1-C_4$ alkoxy, —$SO_2$—$(C_1-C_4)$ alkyl, $CF_3$, or $OCF_3$.

A Preferred class of compounds of formula IV-d include compounds of formula IV-e, wherein $R_2$ is —$(C_1-C_4)$ alkyl-phthalimidyl, optionally fused to a phenyl ring and wherein said phthalimidyl, or phenyl groups are optionally substituted with a total of 1, 2, 3, or 4 groups that are independently halogen, $C_1-C_4$ alkyl, $C_1-C_4$ alkoxy, —$SO_2$—$(C_1-C_4)$ alkyl, $CF_3$, or $OCF_3$.

A Preferred class of compounds of formula IV-c include compounds of formula IV-f, wherein $R_2$ is phenyl, phenyl$(C_1-C_4)$alkyl, or $(C_1-C_6)$alkyl, wherein each phenyl group is optionally substituted with 1, 2, 3, or 4 groups that are independently halogen, $C_1-C_4$ alkyl, $C_1-C_4$ alkoxy, or —$SO_2$—$(C_1-C_4)$ alkyl, $CF_3$ or $OCF_3$.

A Preferred class of compounds of formula IV-f include compounds of formula IV-g, wherein $R_2$ is phenyl or benzyl, wherein each is optionally substituted with 1, 2, 3, or 4 groups that are independently halogen, $C_1-C_4$ alkyl, $C_1-C_4$ alkoxy, —$SO_2$—$(C_1-C_4)$ alkyl, $CF_3$ or $OCF_3$.

A Preferred class of compounds of formula IV-g include compounds of formula IV-h, wherein $R_2$ is phenyl or benzyl, each of which is substituted at position number 3 or 4 of the $R_2$ phenyl ring with a halogen, $CF_3$ or $OCF_3$.

A Preferred class of compounds of formula IV-h include compounds of formula IV-i, wherein $R_2$ is phenyl which is substituted at position number 3 or 4 of the $R_2$ phenyl ring with a halogen, $CF_3$ or $OCF_3$.

A Preferred class of compounds of formula IV-h include compounds of formula IV-j, wherein $R_2$ is benzyl, which is substituted at position number 3 or 4 of the $R_2$ phenyl ring with a halogen, $CF_3$ or $OCF_3$.

A Preferred class of compounds of formula IV-c include compounds of formula IV-k, wherein $L_3$ is a bond, —O—$(C_1-C_4)$alkyl, or —$(C_1-C_4)$ alkyl-;

Q is indolyl, -benzofuranyl-$(C_1-C_4)$ alkyl-phenyl, indolizinyl, benzofuranyl, -indolyl-$(C_1-C_4)$alkyl-phenyl, or dibenzo[b,d]furan, each of which is optionally substituted with 1, 2, 3, or 4 groups that are independently $C_1-C_6$ alkyl, $C_1-C_4$ alkoxycarbonyl, $C_1-C_6$ alkoxy, halogen, $CF_3$ or $OCF_3$.

A Preferred class of compounds of formula IV-k include compounds of formula IV-1, wherein Q is-benzofuranyl-$(C_1-C_4)$ alkyl-phenyl, benzofuranyl, or dibenzo[b,d]furan, each of which is optionally substituted with 1, 2, 3, or 4 groups that are independently $C_1-C_6$ alkyl, $C_1-C_4$ alkoxycarbonyl, $C_1-C_6$ alkoxy, halogen, $CF_3$ or $OCF_3$.

In another aspect, the invention provides a pharmaceutical composition comprising a compounds of according to formula 1 at least one pharmaceutically acceptable solvent, carrier, excipient or adjuvant.

In another aspect, the invention provides a method of treating diabetes in a patient needing such treatment comprising administering a compound of formula 1 or a pharmaceutical composition of comprising a compound of formula I.

In another aspect, the invention provides compounds and pharmaceutically acceptable salts thereof of formula V, i.e., compounds of formula I, wherein n is 0, 1, or 2;

$R_1$ is H, $C_1-C_6$ alkyl, phenyl$(C_1-C_6)$alkyl;

$R_2$ is $C_1-C_6$ alkyl, —$(C_1-C_4)$ alkyl-C(O)$NH_2$, $(C_1-C_4)$ hydroxyalkyl, phenyl, or phenyl$(C_1-C_4)$ alkyl, wherein each phenyl is optionally substituted with 1 or 2 groups that are independently halogen, $C_1-C_4$ alkyl, $C_1-C_4$ alkoxy, —$SO_2$—$(C_1-C_4)$ alkyl, haloalkyl, or haloalkoxy;

$R_{20}$, $R_{21}$, $R_{22}$, and $R_{23}$ are independently selected from H, arylalkyl, arylalkyl, halogen, alkyl, OH, alkoxy, $NO_2$, $NH_2$, $NH(C_1-C_6)$alkyl, $N(C_1-C_6$alkyl) $(C_1-C_6$alkyl), NH-aryl, NHC(O)—($C_1$-$C_4$) alkyl-aryl, N($C_1$-$C_4$ alkyl)C(O)—($C_1$-$C_4$)alkyl-aryl, N($C_1$-$C_4$) alkyl-aryl, —NHSO$_2$-aryl, or —N($C_1$-$C_4$alkyl)SO$_2$aryl, wherein the aryl group is optionally substituted with 1, 2, 3, or 4 groups that are independently $C_1$-$C_6$ alkyl, $C_1$-$C_6$ alkoxy, halogen, OH, NO$_2$, haloalkyl, or haloalkoxy;

L is —SO$_2$N($C_1$-$C_4$)alkyl-, —SO$_2$NH—, —C(O)N($C_1$-$C_4$) alkyl-, —C(O)—($C_1$-$C_4$) alkyl-, —O—, —NH—, or —N($C_1$-$C_4$ alkyl)-, wherein each alkyl group is optionally substituted with phenyl, which is optionally substituted with 1, 2, 3, or 4 groups that are independently $C_1$-$C_6$ alkyl, $C_1$-$C_6$ alkoxy, halogen, OH, NO$_2$, haloalkyl, or haloalkoxy;

$L_3$ is a bond, —($C_1$-$C_4$)alkyl-O—, —O—($C_1$-$C_4$)alkyl, or —($C_1$-$C_4$)alkyl-;

the A-ring is
(a) phenyl substituted with benzofuranyl or dibenzofuranyl, where
the phenyl is optionally substituted with 1, 2, or 3 groups that are independently, halogen, $C_1$-$C_4$ alkyl, $C_1$-$C_4$ alkoxy, $C_1$-$C_4$ haloalkyl, $C_1$-$C_4$ haloalkoxy, NO$_2$, NH$_2$, NH($C_1$-$C_6$)alkyl, or N($C_1$-$C_6$)alkyl($C_1$-$C_6$)alkyl, and
the dibenzofuranyl and benzofuranyl groups are optionally substituted with 1, 2, or 3 groups that are independently $C_1$-$C_6$ alkyl, $C_1$-$C_4$ alkoxycarbonyl, $C_1$-$C_6$ alkoxy, halogen, haloalkyl, haloalkoxy, or NR$_6$R$_7$; where
$R_6$ and $R_7$ are independently H, $C_1$-$C_6$ alkyl, $C_2$-$C_6$ alkanoyl, $C_1$-$C_6$ alkoxycarbonyl, —C(O)NH$_2$, —C(O)NH($C_1$-$C_6$)alkyl, or —C(O)N($C_1$-$C_6$)alkyl($C_1$-$C_6$)alkyl; or
(b) benzofuranyl or dibenzofuranyl, each of which is optionally substituted with 1, 2, or 3 groups that are independently $C_1$-$C_6$ alkyl, $C_1$-$C_4$ alkoxycarbonyl, $C_1$-$C_6$ alkoxy, halogen, haloalkyl, haloalkoxy, NO$_2$, or NR$_6$R$_7$.

In still another aspect, the invention provides compounds of formula V-1, i.e., compounds of formula V wherein R$_1$ is H.

In still another aspect, the invention provides compounds of formula V-2, i.e., compounds of formula V-1 wherein
n is 0 or 1.
R$_{22}$ and R$_{23}$ are both hydrogen; and
R$_{20}$ and R$_{21}$ are independently selected from H, halogen, $C_1$-$C_4$ alkyl, OH, alkoxy, NO$_2$, NH$_2$, NH($C_1$-$C_6$)alkyl, or N($C_1$-$C_6$alkyl) ($C_1$-$C_6$alkyl).

In yet another aspect, the invention provides compounds of formula V-3, i.e., compounds of formula V-2 wherein R$_2$ is phenyl($C_1$-$C_3$)alkyl optionally substituted with 1 or 2 groups that are independently halogen, $C_1$-$C_4$ alkyl, $C_1$-$C_4$ alkoxy, —SO$_2$—($C_1$-$C_4$) alkyl, CF$_3$ or OCF$_3$. In another aspect, R$_2$ is benzyl or phenethyl optionally substituted as above. In still another aspect, R$_2$ is benzyl optionally substituted as above. In yet another aspect, R$_2$ is phenethyl optionally substituted as above. In still another aspect the R$_2$ group is unsubstituted or monosubstituted.

In yet another aspect, the invention provides compounds of formula V-4, i.e., compounds of formula V-3 wherein R$_2$ is unsubstituted or mono substituted benzyl.

In another aspect, preferred compounds of formula V include the compounds of formula VI,

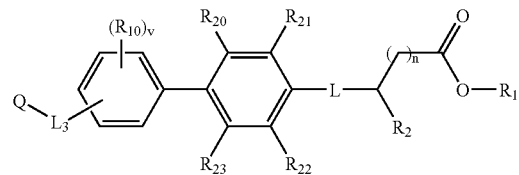

wherein
R$_1$ is H or $C_1$-$C_2$ alkyl;
R$_2$ is phenyl, phenyl($C_1$-$C_4$) alkyl (such as benzyl, phenethyl, or —(CH$_2$)$_4$-phenyl)), wherein each phenyl group is optionally substituted with 1, 2, or 3 groups that are independently halogen, hydroxy, $C_1$-$C_4$ alkyl, $C_1$-$C_4$ alkoxy, ($C_1$-$C_4$) haloalkyl, or ($C_1$-$C_4$)haloalkoxy;
v is 0, 1, or 2;
each R$_{10}$ is independently hydroxy, halogen, $C_1$-$C_4$ alkyl, $C_1$-$C_4$ alkoxy, $C_1$-$C_4$ haloalkyl, $C_1$-$C_4$ haloalkoxy, NO$_2$, NH$_2$, NH($C_1$-$C_6$)alkyl, or N($C_1$-$C_6$)alkyl($C_1$-$C_6$)alkyl; and
$L_3$ is a bond, —O—($C_1$-$C_2$)alkyl, or —($C_1$-$C_2$) alkyl-;
Q is benzofuranyl or dibenzofuranyl, each of which is optionally substituted with 1, 2 or 3 groups that are independently $C_1$-$C_6$ alkyl, $C_1$-$C_6$ alkoxy, halogen, $C_1$-$C_3$ haloalkyl, $C_1$-$C_3$ haloalkoxy, NO$_2$, or NR$_6$R$_7$; where R$_6$ and R$_7$ are independently H or $C_1$-$C_6$ alkyl.

In one aspect, the invention provides compounds of formula VI-1, i.e., compounds of formula VI wherein
R$_2$ is phenyl, benzyl, or phenethyl, where the phenyl portion of each is optionally substituted with 1 or 2 groups that are independently halogen, $C_1$-$C_4$ alkyl, $C_1$-$C_4$ alkoxy, CF$_3$ or OCF$_3$; and
R$_{20}$, R$_{21}$, R$_{22}$, and R$_{23}$ are independently selected from H, halogen, alkyl, OH, alkoxy, NO$_2$, NH$_2$, NH($C_1$-$C_6$)alkyl, or N($C_1$-$C_6$alkyl) ($C_1$-$C_6$alkyl).

In another aspect, the invention provides compounds of formula VI-2, i.e., compounds of formula VI-1 wherein R$_{22}$ and R$_{23}$ are both hydrogen.

In yet another aspect, the invention provides compounds of formula VI-3, i.e., compounds of formula VI-2 wherein R$_1$ and R$_6$ are hydrogen; and v is 0 or 1.

In still another aspect, the invention provides compounds of formula VI-4, i.e., compounds of formula VI-1, VA-2, or VI-3 wherein $L_3$ is a bond.

In yet still another aspect, the invention provides compounds of formula VII, i.e., compounds of formula VI-4 with the following structure:

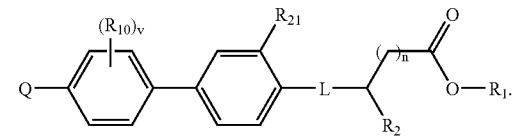

In another aspect, the invention provides compounds of formula VII-1, i.e., compounds of formula VII wherein R$_1$ is H; and R$_{21}$ is H, NO$_2$, $C_1$-$C_6$ alkyl (in another aspect, $C_1$-$C_4$ alkyl), or halogen.

In still another aspect, the invention provides compounds of formula VII-2, i.e., compounds of formula VII-1 wherein L is —C(O)—($C_1$-$C_4$) alkyl-.

In yet another aspect, the invention provides compounds of formula VII-3, i.e., compounds of formula VII-2 wherein Q is benzofuranyl or dibenzofuranyl, each of which is optionally substituted with 1 or 2 groups that are independently $C_1$-$C_4$ alkyl, halogen, or $C_1$-$C_3$ haloalkyl (in one aspect, $CF_3$.)

In another aspect, the invention provides compounds of formula VII-4, i.e., compounds according to any one of formulas VII, VII-1, VII-2, VII-3, wherein $R_2$ is phenyl, benzyl, or phenethyl (more preferably, phenyl or benzyl), where the phenyl portion of each is optionally substituted with 1 or 2 groups that are independently halogen, $C_1$-$C_4$ alkyl (in one aspect methyl or ethyl), $C_1$-$C_4$ alkoxy (in one aspect, methoxy or ethoxy), $CF_3$ or $OCF_3$. In a different aspect, $R_2$ is unsubstituted. In still another aspect, $R_2$ is monosubstituted at the 3 or 4 position.

In yet still another aspect, the invention provides compounds of formula VIII, i.e., compounds of formula VI with the following structure:

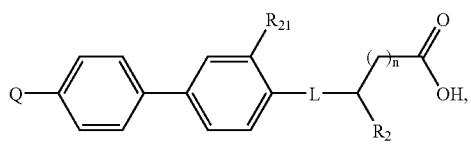

where n is 0 or 1.

In another aspect, the invention provides compounds of formula VIII-1, i.e., compounds of formula VIII wherein $R_{21}$ is H, $NO_2$, $C_1$-$C_4$ alkyl, or halogen.

In still another aspect, the invention provides compounds of formula VIII-2, i.e., compounds of formula VIII-1 or formula VIII wherein Q is benzofuranyl or dibenzofuranyl, each of which is optionally substituted with 1 or 2 groups that are independently $C_1$-$C_4$ alkyl, halogen, or $C_1$-$C_3$ haloalkyl (in one aspect, $CF_3$.)

In yet another aspect, the invention provides compounds of formula VIII-3, i.e., compounds of formula VIII, VIII-1, or VIII-2, wherein $R_2$ is phenyl, benzyl, or phenethyl (more preferably, phenyl or benzyl), where the phenyl portion of each is optionally substituted with 1 or 2 groups that are independently halogen, $C_1$-$C_4$ alkyl (in one aspect methyl or ethyl), $C_1$-$C_4$ alkoxy (in one aspect, methoxy or ethoxy), $CF_3$ or $OCF_3$. In a different aspect, $R_2$ is unsubstituted. In still another aspect, $R_2$ is monosubstituted at the 3 or 4 position.

In yet another aspect, the invention provides compounds of formula VIII-4, i.e., compounds of formula VIII, VIII-1, VIII-2, or VIII-3, wherein L is —C(O)—($C_1$-$C_4$) alkyl-.

In yet another aspect, the invention provides compounds of formula VIII-5, i.e., compounds of formula VIII, VIII-1, VIII-2, or VIII-3, wherein L is —O—.

In yet another aspect, the invention provides compounds of formula VIII-6, i.e., compounds of formula VIII, VIII-1, VIII-2, or VIII-3, wherein L is —NH—, or N($C_1$-$C_4$ alkyl)-.

In yet another aspect, the invention provides compounds of formula VIII-7, i.e., compounds of formula VIII, VIII-1, VIII-2, or VIII-3, wherein L is —$SO_2$NH— or —$NHSO_2$—.

In yet another aspect, the invention provides compounds of formula VIII-8, i.e., compounds of formula VIII, VIII-1, VIII-2, or VIII-3, wherein L is —$SO_2$N($C_1$-$C_4$ alkyl)-.

In yet another aspect, the invention provides compounds of formula VIII-9, i.e., compounds of formula VIII-4, VIII-5, VIII-6, VIII-7, or VIII-8, wherein n is 0.

In yet another aspect, the invention provides compounds of formula VIII-10, i.e., compounds of formula VIII-4, VIII-5, VIII-6, VIII-7, or VIII-8, wherein n is 1.

In yet another aspect, the invention provides compounds of formula VIII-11, i.e., compounds of formula VIII-9, wherein $R_2$ is phenyl.

In yet another aspect, the invention provides compounds of formula VIII-12, i.e., compounds of formula VIII-10, wherein $R_2$ is phenyl.

In yet another aspect, the invention provides compounds of formula VIII-13, i.e., compounds of formula VIII-9, wherein $R_2$ is benzyl.

In yet another aspect, the invention provides compounds of formula VIII-14, i.e., compounds of formula VIII-10, wherein $R_2$ is benzyl.

In another aspect, the invention provides a method of treating diabetes, comprising administering to a patient in need of such treatment a pharmaceutically acceptable amount of a compound of formula I, or any of the preceding formulas.

In another aspect, the invention encompasses a method of treating diabetes comprising administering to a patient in need thereof, a pharmaceutically acceptable amount of a compound or salt of formula I or a pharmaceutical composition comprising a compound or salt of formula I, or any of the preceding formulas.

In another aspect, the invention encompasses a method of inhibiting TPT-1B comprising administering to a patient in need thereof, a pharmaceutically acceptable amount of a compound or salt of formula I, or any of the preceding formulas or a pharmaceutical composition comprising a compound or salt of formula I, or any of the preceding formulas.

In another aspect, the invention encompasses a method of treating cancer or neurodegenerative diseases comprising administering to a patient in need thereof, a pharmaceutically acceptable amount of a compound or salt of formula I, or any of the preceding formulas or a pharmaceutical composition comprising a compound or salt of formula I, or any of the preceding formulas.

Illustrative compounds of the invention include the following, which were named using ChemDraw v. 6.02, which is sold by Cambridgesoft.com in Cambridge, Mass., or using Name Pro IUPAC Naming Software, version 5.09, available from Advanced Chemical Development, Inc., 90 Adelaide Street West, Toronto, Ontario, M5H 3V9, Canada.

methyl {[4'-(1-benzofuran-2-yl)biphenyl-4-yl]oxy} (phenyl)acetate

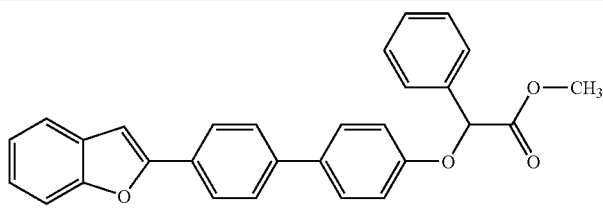

| | |
|---|---|
| methyl ({4'-[(3-benzoylphenoxy)methyl]biphenyl-4-yl}oxy) (phenyl)acetate | 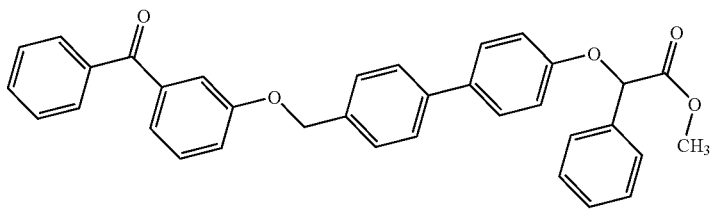 |
| N-[4'-(2-benzyl-4-fluoro-1-benzofuran-3-yl)-3-nitrobiphenyl-4-yl]phenylalanine | 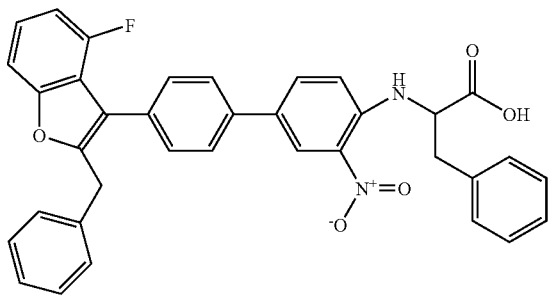 |
| 2-({[4'-(2-benzyl-1-benzofuran-3-yl)biphenyl-4-yl]sulfonyl}amino)butanoic acid | 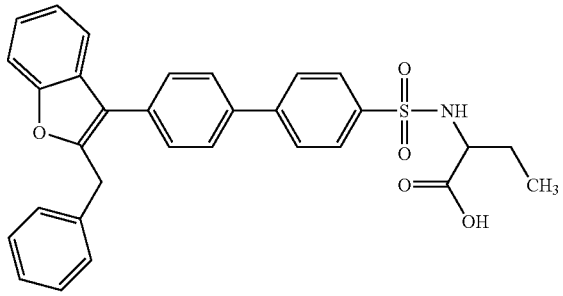 |
| 4-(4'-dibenzo[b,d]furan-4-ylbiphenyl-4-yl)-4-oxo-2-[3-(trifluoromethyl)benzyl]butanoic acid | 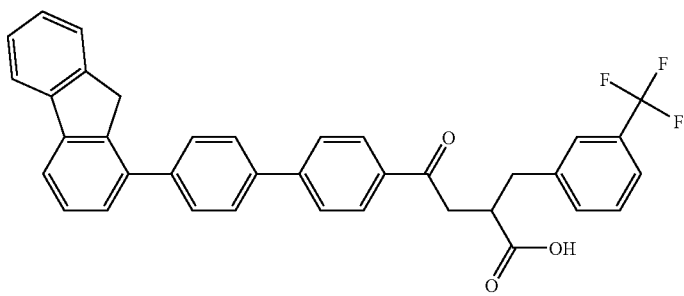 |

As noted above, the compounds of the invention bind to and preferably, inhibit PTP-1B. As a result that are useful in the treatment of various diseases, including controlling or treating Type 2 diabetes, improving glucose tolerance, and in improving insulin sensitivity in patients in need thereof. The compounds are also useful in treating or controlling other PTP-1B mediated diseases, such as the treatment of cancer, neurodegenerative diseases and the like.

The term "alkoxy" represents an alkyl group of indicated number of carbon atoms attached to the parent molecular moiety through an oxygen bridge. Examples of alkoxy groups include, for example, methoxy, ethoxy, propoxy and isopropoxy.

As used herein, the term "alkyl" includes those alkyl groups of a designed number of carbon atoms. Alkyl groups may be straight, or branched. Examples of "alkyl" include methyl, ethyl, propyl, isopropyl, butyl, iso-, sec- and tert-butyl, pentyl, hexyl, heptyl, 3-ethylbutyl, and the like.

The term "aryl" refers to an aromatic hydrocarbon ring system containing at least one aromatic ring. The aromatic ring may optionally be fused or otherwise attached to other aromatic hydrocarbon rings or non-aromatic hydrocarbon rings. Examples of aryl groups include, for example, phenyl, naphthyl, 1,2,3,4-tetrahydronaphthalene and biphenyl. Preferred examples of aryl groups include phenyl, naphthyl, and anthracenyl. More preferred aryl groups are phenyl and naphthyl. Most preferred is phenyl.

The term "cycloalkyl" refers to a $C_3$-$C_8$ cyclic hydrocarbon. Examples of cycloalkyl include cyclopropyl, cyclobutyl, cyclopentyl, cyclohexyl, cycloheptyl and cyclooctyl.

The terms "halogen" or "halo" indicate fluorine, chlorine, bromine, and iodine.

The term "heterocycloalkyl," refers to a ring or ring system containing at least one heteroatom selected from nitrogen, oxygen, and sulfur, wherein said heteroatom is in a non-aromatic ring. The heterocycloalkyl ring is optionally fused to or otherwise attached to other heterocycloalkyl rings and/or non-aromatic hydrocarbon rings and/or phenyl rings. Preferred heterocycloalkyl groups have from 3 to 7 members. Examples of heterocycloalkyl groups include, for example, 1,2,3,4-tetrahydroisoquinoline, piperazine, morpholine, piperidine, tetrahydrofuran, pyrrolidine, pyridinonyl, and pyrazole. Preferred heterocycloalkyl groups include piperidinyl, piperazinyl, morpholinyl, pyrrolidinyl, pyridinonyl, dihydropyrrolidinyl, and pyrrolidinonyl.

The term "heteroaryl" refers to an aromatic ring containing at least one heteroatom selected from nitrogen, oxygen, and sulfur. The heteroaryl ring may be fused or otherwise attached to one or more heteroaryl rings, aromatic or non-aromatic hydrocarbon rings or heterocycloalkyl rings. Examples of heteroaryl groups include, for example, pyridine, furan, thienyl, 5,6,7,8-tetrahydroisoquinoline and pyrimidine. Preferred examples of heteroaryl groups include thienyl, benzothienyl, pyridyl, quinolyl, pyrazolyl, pyrimidyl, imidazolyl, benzimidazolyl, furanyl, benzofuranyl, dibenzofuranyl, thiazolyl, benzothiazolyl, isoxazolyl, oxadiazolyl, isothiazolyl, benzisothiazolyl, triazolyl, pyrrolyl, indolyl, pyrazolyl, and benzopyrazolyl.

The compounds of this invention may contain one or more asymmetric carbon atoms, so that the compounds can exist in different stereoisomeric forms. These compounds can be, for example, racemates, chiral non-racemic or diastereomers. In these situations, the single enantiomers, i.e., optically active forms, can be obtained by asymmetric synthesis or by resolution of the racemates. Resolution of the racemates can be accomplished, for example, by conventional methods such as crystallization in the presence of a resolving agent; chromatography, using, for example a chiral HPLC column; or derivatizing the racemic mixture with a resolving reagent to generate diastereomers, separating the diastereomers via chromatography, and removing the resolving agent to generate the original compound in enantiomerically enriched form. Any of the above procedures can be repeated to increase the enantiomeric purity of a compound.

When the compounds described herein contain olefinic double bonds or other centers of geometric asymmetry, and unless otherwise specified, it is intended that the compounds include the cis, trans, Z- and E-configurations. Likewise, all tautomeric forms are also intended to be included.

The compounds of general Formula I may be administered orally, topically, parenterally, by inhalation or spray or rectally in dosage unit formulations containing conventional non-toxic pharmaceutically acceptable carriers, adjuvants and vehicles. The term parenteral as used herein includes percutaneous, subcutaneous, intravascular (e.g., intravenous), intramuscular, or intrathecal injection or infusion techniques and the like. In addition, there is provided a pharmaceutical formulation comprising a compound of general Formula I and a pharmaceutically acceptable carrier. One or more compounds of general Formula I may be present in association with one or more non-toxic pharmaceutically acceptable carriers and/or diluents and/or adjuvants, and if desired other active ingredients. The pharmaceutical compositions containing compounds of general Formula I may be in a form suitable for oral use, for example, as tablets, troches, lozenges, aqueous or oily suspensions, dispersible powders or granules, emulsion, hard or soft capsules, or syrups or elixirs.

Compositions intended for oral use may be prepared according to any method known to the art for the manufacture of pharmaceutical compositions and such compositions may contain one or more agents selected from the group consisting of sweetening agents, flavoring agents, coloring agents and preservative agents in order to provide pharmaceutically elegant and palatable preparations. Tablets contain the active ingredient in admixture with non-toxic pharmaceutically acceptable excipients that are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques. In some cases such coatings may be prepared by known techniques to delay disintegration and absorption in the gastrointestinal tract and thereby provide a sustained action over a longer period. For example, a time delay material such as glyceryl monosterate or glyceryl distearate may be employed.

Formulations for oral use may also be presented as hard gelatin capsules, wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Formulations for oral use may also be presented as lozenges.

Aqueous suspensions contain the active materials in admixture with excipients suitable for the manufacture of aqueous suspensions. Such excipients are suspending agents, for example sodium carboxymethylcellulose, methylcellulose, hydropropyl-methylcellulose, sodium alginate, polyvinylpyrrolidone, gum tragacanth and gum acacia; dispersing or wetting agents may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions may be formulated by suspending the active ingredients in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents and flavoring agents may be added to provide palatable oral preparations. These compositions may be preserved by the addition of an antioxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents or suspending agents are exemplified by those already mentioned above. Additional excipients, for example sweetening, flavoring and coloring agents, may also be present.

Pharmaceutical compositions of the invention may also be in the form of oil-in-water emulsions. The oily phase may be a vegetable oil or a mineral oil or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol, anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol, glucose or sucrose. Such formulations may also contain a demulcent, a preservative and flavoring and coloring agents. The pharmaceutical compositions may be in the form of a sterile injectable aqueous or oleaginous suspension. This suspension may be formulated according to the known art using those suitable dispersing or wetting agents and suspending agents that have been mentioned above. The sterile injectable preparation may also be a sterile injectable solution or suspension in a non-toxic parentally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono-or diglycerides. In addition, fatty acids such as oleic acid find use in the preparation of injectables.

The compounds of general Formula I may also be administered in the form of suppositories, e.g., for rectal administration of the drug. These compositions can be prepared by mixing the drug with a suitable non-irritating excipient that is solid at ordinary temperatures but liquid at the rectal temperature and will therefore melt in the rectum to release the drug. Such materials include cocoa butter and polyethylene glycols.

Compounds of general Formula I may be administered parenterally in a sterile medium. The drug, depending on the vehicle and concentration used, can either be suspended or dissolved in the vehicle. Advantageously, adjuvants such as local anesthetics, preservatives and buffering agents can be dissolved in the vehicle.

For disorders of the eye or other external tissues, e.g., mouth and skin, the formulations are preferably applied as a topical gel, spray, ointment or cream, or as a suppository, containing the active ingredients in a total amount of, for example, 0.075 to 30% w/w, preferably 0.2 to 20% w/w and most preferably 0.4 to 15% w/w. When formulated in an ointment, the active ingredients may be employed with either paraffinic or a water-miscible ointment base.

Alternatively, the active ingredients may be formulated in a cream with an oil-in-water cream base. If desired, the aqueous phase of the cream base may include, for example at least 30% w/w of a polyhydric alcohol such as propylene glycol, butane-1,3-diol, mannitol, sorbitol, glycerol, polyethylene glycol and mixtures thereof. The topical formulation may desirably include a compound which enhances absorption or penetration of the active ingredient through the skin or other affected areas. Examples of such dermal penetration enhancers include dimethylsulfoxide and related analogs. The compounds of this invention can also be administered by a transdermal device. Preferably topical administration will be accomplished using a patch either of the reservoir and porous membrane type or of a solid matrix variety. In either case, the active agent is delivered continuously from the reservoir or microcapsules through a membrane into the active agent permeable adhesive, which is in contact with the skin or mucosa of the recipient. If the active agent is absorbed through the skin, a controlled and predetermined flow of the active agent is administered to the recipient. In the case of microcapsules, the encapsulating agent may also function as the membrane. The transdermal patch may include the compound in a suitable solvent system with an adhesive system, such as an acrylic emulsion, and a polyester patch. The oily phase of the emulsions of this invention may be constituted from known ingredients in a known manner. While the phase may comprise merely an emulsifier, it may comprise a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make-up the so-called emulsifying wax, and the wax together with the oil and fat make up the so-called emulsifying ointment base which forms the oily dispersed phase of the cream formulations. Emulsifiers and emulsion stabilizers suitable for use in the formulation of the present invention include Tween 60, Span 80, cetostearyl alcohol, myristyl alcohol, glyceryl monostearate, and sodium lauryl sulfate, among others. The choice of suitable oils or fats for the formulation is based on achieving the desired cosmetic properties, since the solubility of the active compound in most oils likely to be used in pharmaceutical emulsion formulations is very low. Thus, the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters may be used. These may be used alone or in combination depending on the properties required. Alternatively, high melting point lipids such as white soft paraffin and/or liquid paraffin or other mineral oils can be used.

Formulations suitable for topical administration to the eye also include eye drops wherein the active ingredients are dissolved or suspended in suitable carrier, especially an aqueous solvent for the active ingredients. The antiinflammatory active ingredients are preferably present in such formulations in a concentration of 0.5 to 20%, advantageously 0.5 to 10% and particularly about 1.5% w/w. For therapeutic purposes, the active compounds of this combination invention are ordinarily combined with one or more adjuvants appropriate to the indicated route of administration. If administered per os, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose. Formulations for parenteral administration may be in the form of aqueous or non-aqueous isotonic sterile injection solutions or suspensions. These solutions and suspensions may be prepared from sterile powders or granules having one or more of the carriers or diluents mentioned for use in the formulations for oral administration. The compounds may be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

Dosage levels of the order of from about 0.1 mg to about 140 mg per kilogram of body weight per day are useful in the treatment of the above-indicated conditions (about 0.5 mg to about 7 g per patient per day). The amount of active ingredient that may be combined with the carrier materials to produce a single dosage form will vary depending upon the host treated and the particular mode of administration. Dosage unit forms will generally contain between from about 1 mg to about 500 mg of an active ingredient. The daily dose can be administered in one to four doses per day. In the case of skin conditions, it may be preferable to apply a topical preparation of compounds of this invention to the affected area two to four times a day.

It will be understood, however, that the specific dose level for any particular patient will depend upon a variety of factors including the activity of the specific compound employed, the age, body weight, general health, sex, diet, time of administration, route of administration, and rate of excretion, drug combination and the severity of the particular disease undergoing therapy.

For administration to non-human animals, the composition may also be added to the animal feed or drinking water. It may be convenient to formulate the animal feed and drinking water compositions so that the animal takes in a therapeutically appropriate quantity of the composition along with its diet. It may also be convenient to present the composition as a premix for addition to the feed or drinking water. Preferred non-human animals include domesticated animals.

As noted above, the invention also provides methods and compositions for combination therapy of Type I and Type II diabetes. In one such aspect, the invention provides methods of using compounds of formula I in combination with one or more angiotensin converting enzyme (ACE) inhibitors for improving the cardiovascular risk profile in patients experiencing or subject to Syndrome X or type II diabetes (non-insulin-dependent diabetes mellitus), preferably in human type II diabetics. These methods may also be characterized as the reduction of risk factors for heart disease, stroke or heart attack in a type II diabetic.

These methods include the reduction of hyperlipidemia in a patients experiencing or subject to Syndrome X or type II diabetes. These methods include methods lowering low density lipoprotein (LDL) blood levels and to increase high density lipoprotein (HDL) blood levels. The methods herein may further be characterized as useful for inhibiting, preventing or reducing atherosclerosis in a type II diabetics, or for reducing the risk factors thereof.

These methods also include the lowering of free fatty acid blood levels and triglyceride levels in type II diabetics.

Among the ACE inhibitors which may be utilized with the invention described herein are quinapril, ramipril, verapamil, captopril, diltiazem, clonidine, hydrochlorthiazide, benazepril, prazosin, fosinopril, lisinopril, atenolol, enalapril, perindropril, perindropril tert-butylamine, trandolapril and moexipril, or a pharmaceutically acceptable salt form of one or more of these compounds.

The invention also provides methods of using PTPase inhibitors of formula I for improving the cardiovascular or cerebrovascular risk profile in patients experiencing or subject to type II diabetes (non-insulin-dependent diabetes mellitus), preferably in human type II diabetics or a patient experiencing or subject to Syndrome X. These methods may also be characterized as the reduction of risk factors for heart disease, stroke or heart attack in a type II diabetic or a patient experiencing or subject to Syndrome X.

The invention also provides methods of using a pharmacological combination of one or more PTPase inhibiting agents, one or more biguanide agents, and, optionally one or more sulfonylurea agents for treatment of type II diabetes or Syndrome X in a patient in need of such treatment. Also provided are methods of using these agents to treat or inhibit metabolic disorders mediated by insulin resistance or hyperglycemia in a patient in need thereof. Further included in this invention is a method of modulating blood glucose levels in a patient in need thereof.

Each of these methods comprises administering to a patient in need thereof pharmaceutically effective amounts of:

a) a PTPase inhibiting agent of formula I; and
b) a biguanide agent; and
c) optionally, a sulfonylurea agent.

Biguanide agents useful with this invention include metformin and its pharmaceutically acceptable salt forms. Sulfonylurea agents useful for the methods and combinations of this invention may be selected from the group of glyburide, glyburide, glipizide, glimepiride, chlorpropamide, tolbutamide, or tolazamide, or a pharmaceutically acceptable salt form of these agents.

This invention also provides pharmaceutical compositions and methods of using PTPase inhibitors of formula I in combination with one or more alpha-glucosidase inhibitors, such as miglitol or acarbose, for improving the cardiovascular risk profile in patients experiencing or subject to Syndrome X or type II diabetes (non-insulin-dependent diabetes mellitus), preferably in human type II diabetics. These methods may also be characterized as the reduction of risk factors for heart disease, stroke or heart attack in a patient in such need.

These methods include the reduction of hyperlipidemia in type II diabetics, including methods in type II diabetics for lowering low density lipoprotein (LDL) blood levels and to increase high density lipoprotein (HDL) blood levels. The methods herein may further be characterized as useful for inhibiting, preventing or reducing atherosclerosis in a type II diabetic or a patient experiencing or subject to Syndrome X, or the risk factors of either.

These methods also include the lowering free fatty acid blood levels and triglyceride levels in type II diabetics, or a patient experiencing or subject to Syndrome X.

Among the alpha-glucosidase inhibitors which may be utilized with the invention described herein are miglitol or acarbose, or a pharmaceutically acceptable salt form of one or more of these compounds.

This invention further provides methods for using a PTPase inhibitor of the invention and a sulfonylurea agent for the management of Syndrome X or type 2 diabetes and for improving the cardiovascular risk profile in patients experiencing or subject to those maladies. These methods may also be characterized as the reduction of risk factors in such patients for heart disease, stroke or heart attack in a type II diabetic. Such methods include the reduction of hyperlipidemia in a patients experiencing or subject to Syndrome X or type II diabetes and include methods for lowering low density lipoprotein (LDL) blood levels, high density lipoprotein (HDL) blood levels, and overall blood lipoprotein levels. The methods herein may further be characterized as inhibiting, preventing or reducing atherosclerosis in patients subject to or experiencing Syndrome X or type II diabetes, or the risk factors thereof. Such methods further include the lowering of free fatty acid blood levels and triglyceride levels in such patients.

Representative sulfonylurea agents include glipizide, glyburide (glibenclamide), chlorpropamide, tolbutamide, tolazamide and glimepriride, or the pharmaceutically acceptable salt forms thereof.

In addition, the invention provides combinations of a PTPase inhibitor of the invention and at least one thiazolidinedione agents. Such combinations are useful for treatment, inhibition or maintenance of Syndrome X or type II diabetes in patients in need of such treatment. Accordingly, methods of using such combinations are provided by the invention. Thus, the invention provides methods of using these agents to treat or inhibit metabolic disorders mediated by insulin resistance or hyperglycemia in patients in need thereof. Further included in this invention are methods of modulating blood glucose levels in a patient in need thereof.

Each of these methods comprises administering to a patient in need thereof pharmaceutically effective amounts of:
 a) a thiazolidinedione agent, such as selected from the group of pioglitazone and rosiglitazone, or a pharmaceutically acceptable salt form of these agents; and
 b) a compound of formula I.

The invention also provides pharmaceutical compositions and methods of using PTPase inhibitors in combination with one or more antilipemic agents. Such methods and compositions are useful for improving the cardiovascular risk profile in patients experiencing or subject to type II diabetes (non-insulin-dependent diabetes mellitus), preferably in type II diabetics or Syndrome X. These methods also include reducing the risk factors for heart disease, stroke or heart attack in a type II diabetic or a patient experiencing or subject to Syndrome X. Such methods further include the reduction of hyperlipidemia in type II diabetics, including such methods in type II diabetics for lowering low density lipoprotein (LDL) blood levels and to increase high density lipoprotein (HDL) blood levels. These compositions and methods are also useful for inhibiting, preventing or reducing atherosclerosis in a type II diabetic or a patient experiencing or subject to Syndrome X, or the risk factors thereof. In this aspect, the compositions and methods are useful for lowering of free fatty acid blood levels and triglyceride levels in type II diabetics, or patients experiencing or subject to Syndrome X.

Representative antilipemic or agents, also known as antihyperlipidemic agents, suitable for use in the invention are bile acid sequestrants, fibric acid derivatives, HMG-COA reductase inhibitors and nicotinic acid compounds. Bile acid sequestrant agents useful with this invention include colestipol and colesevelam, and their pharmaceutically acceptable salt forms. Fibric acid derivatives which may be used with the present invention include clifofibrate, gemfibrozil and fenofibrate. HMG-CoA reductase inhibitors, also known as statins, useful with this invention include cerivastatin, fluvastatin, atorvastatin, lovastatin, pravastatin and simvastatin, or the pharmaceutically acceptable salt forms thereof. Niacin is an example of a nicotinic acid compound which may be used with the methods of this invention. Also useful are lipase inhibiting agents, such as orlistat.

This invention also provides pharmaceutical compositions that are a combination of a compound of Formula I and an aldose reductase inhibitor (ARI). Such combinations are useful in methods for treating, inhibiting or preventing type II diabetes, or its related and associated symptoms, disorders and maladies. These methods comprise administering to a patient in need of such therapy a pharmaceutically effective amount of a composition comprising a combination of pharmaceutically effective amounts of a compound of formula I and an ARI. These compositions and methods are useful for the treatment, prevention or inhibition of diabetic neuropathy, diabetic nephropathy, retinopathy, keratopathy, diabetic uveitis, cataracts.

Representative suitable ARIs are disclosed in U.S. Pat. Nos. 6,420,426 and 6,214,991.

Combinations of the compounds of Formula I and an ARI are also useful for inhibition or reduction of risk factors for heart disease, stroke or heart attack in a type II diabetic. Therefore, in this aspect the invention is useful for reducing hyperlipidemia and/or low density lipoprotein (LDL) blood levels in type II diabetics. Also included in this aspect are methods for inhibiting, preventing or reducing atherosclerosis or the risk factors thereof in type II diabetics. This aspect includes lowering of free fatty acid blood levels and triglyceride levels.

This invention also provides methods of using a compound of formula I and insulin(s) for the management of type I or type II diabetes. Accordingly, the invention provides for combination therapy, i.e., where a compound of Formula I is administered in combination with insulin. Such combination therapy encompasses simultaneous or sequential administration of the compound of Formula I and insulin. The insulins useful in this aspect include both naturally occurring and synthetic insulins.

Insulins useful with the methods and combinations of this invention include rapid acting insulins, intermediate acting insulins, long acting insulins and combinations of intermediate and rapid acting insulins.

Rapid acting commercially available insulin products include HUMALOG® Brand Lispro Injection (rDNA origin); HUMULIN® Regular Human Injection, USP [rDNA origin]; HUMULIN® Regular U-500 Concentrated Human Injection, USP [rDNA origin]; REGULAR ILETIN® II (insulin injection, USP, purified pork) available from Eli Lilly and Co.; and the NOVALIN® Human Insulin Injection and VENOSULIN® BR Buffered Regular Human Injection, each available from Novo Nordisk Pharmaceuticals.

Commercially available intermediate acting insulins useful with this invention include, but are not limited to, the HUMULIN® L brand LENTE® human insulin [rDNA origin] zinc suspension, HUMULIN® N NPH human insulin [rDNA origin] isophane suspension, LENTE® ILETIN.R™. II insulin zinc suspension, USP, purified pork, and NPH ILETIN® II isophane insulin suspension, USP, purified pork, available from Eli Lilly and Company, LANTUS® insulin glargine [rDNA origin] injection, available from Aventis Pharmaceuticals, and the NOVOLIN L Lente® human insulin zinc suspension (recombinant DNA origin), and NOVOLIN® N NPH human insulin isophane suspension (recombinant DNA origin) products available from Novo Nordisk Pharmaceuticals, Inc., Princeton N.J.

Also useful with the methods and formulations of this invention are intermediate and rapid acting insulin combinations, such as the HUMALOG® Mix 75/25 (75% Insulin Lispro Protamine Suspension and 25% Insulin Lispro Injection), HUMULIN® 50/50 (50% Human Insulin Isophane Suspension and 50% Human Insulin Injection) and HUMULIN® 70/30 (70% Human Insulin Isophane Suspension and 30% Human Insulin Injection), each available from Eli Lilly and Company. Also useful are the NOVALIN® 70/30 (70% NPH, Human Insulin Isophane Suspension and 30% Regular, Human Insulin Injection) line of combination products available from Novo Nordisk Pharmaceuticals.

A commercially available long acting insulin for use with this invention is the HUMULIN® U Ultralente® human insulin [rDNA origin] extended zinc suspension, available from Eli Lilly and Company.

Also useful in the methods of this invention are inhaled insulin products, such as the EXUBERA® inhaled insulin product developed by Pfizer Inc. and Aventis SA.

Each of these insulin products can be administered as directed by a medical professional using administrations, dosages and regimens known in the art, such as those published for each product in the Physicians' Desk Reference, 55 Edition, 2001, published by Medical Economics Company, Inc. at Montvale, N.J., the relevant sections of which are incorporated herein by reference. In this aspect, the invention includes, for example, methods for improving the cardiovascular and cerebrovascular risk profiles in patients experiencing or subject to type I or type II diabetes (non-insulin-dependent diabetes mellitus), preferably in human type II diabetics. These methods may also be characterized as the inhibition or reduction of risk factors for heart disease, stroke or heart attack in a type II diabetic.

The compounds of the present invention may be prepared by use of known chemical reactions and procedures. Representative methods for synthesizing compounds of the invention are presented below. It is understood that the nature of the substituents required for the desired target compound often determines the preferred method of synthesis. All variable groups of these methods are as described in the generic description if they are not specifically defined below.

Methods of Preparation

Compounds with a variety of L linkers (Formula I) can be prepared using the chemistry described in general scheme I. Here aryl or heteroaryl bromide E-1 is coupled to intermediate E-2 containing a functional group X that can be modified to provide the desired L-CO$_2$R substituent. The initial coupling reaction between intermediates E-1 and E-2 can often be carried out using a transition metal coupling reaction. Some of the most useful reactions of this type include the Suzuki, Stille and Negishi reactions. Alternatively, for some examples, it may be more convenient to reverse the coupling functional groups such that metal-M is on the E-1 intermediate and the halogen, preferable Br or I, is on the E-2 intermediate. A variety of X substituents may be useful for preparing compounds with a specific L$_1$—CO$_2$R group. Some useful X substituents include sulfonamides, acids, esters, aldehydes, ketones, amides, nitro groups, anilino groups, hydroxyl groups, sulfides and halides. Some examples of targets compounds prepared from intermediate E-3 with X equal to aldehyde or ketone are illustrated in scheme E.

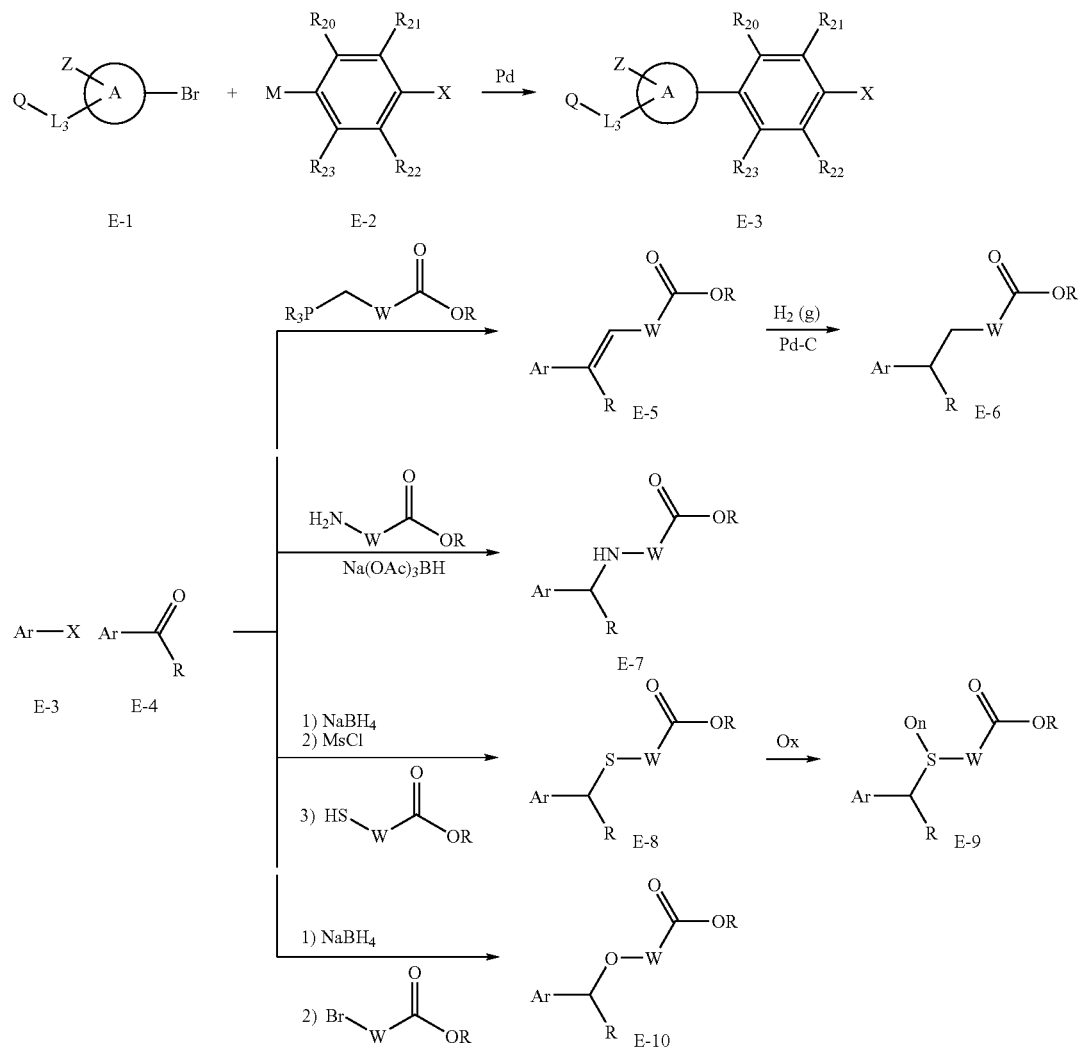

Scheme I

Treatment of carbonyl compound E-4 with a Witting type reagent provides the unsaturated derivative E-5. If the saturated compound E-6 is required, simple hydrogenation with, for example, palladium on carbon can be used. In some cases the carboxylic acid moiety (R═H) may need to be protected as an ester to facilitate the reactions in the scheme. Carbonyl compound E-4 can also be coupled with an amine derivative using a reducing agent like sodium triacetoxyborohydride in a reductive amination reaction to give the corresponding amine E-7. Reduction of aldehyde or ketone E-4 with sodium borohydride gives the corresponding alcohol. Subsequent conversion of this alcohol to a leaving group such as a mesylate or halide followed be displacement with a nucleophile such as a thiol gives sulfide E-8, which if desired can be oxidized to form the sulfoxide or sulfone. Similarly, the same mesylate or halogen leaving group can be displaced by other nucleophiles like amines or alcohols to give the corresponding amine and ether linkers. The sodium borohydride reduction product can also be coupled directly to an alkyl halide or substituted phenol using simple alkylation or Mitsunobu conditions respectively.

One method for the preparation of compounds wherein L is —C(O)-alkyl-is disclosed in Scheme II. In this scheme, the malonate, II-b, is reacted with the halide, II-a, to form the coupled product, II-c, which is then coupled to II-d via a transition metal mediated reaction. One of skill in the art will recognized that various bases may be employed to effect the coupling of II-a to II-b and that the phenyl group in II-b may be substituted with a variety of groups. Furthermore, the structure of II-d is not limited to dibenzofurans, nor is the function group on II-d limited to boron derivates; halides, and various sulfonates are also useful. Likewise, other coupling reactions, such as the Heck or Stille reactions, are also useful for carrying out the coupling of II-c to II-d. II-e is then hydrolyzed to form the di-acid, which is then decarboxylated to generate the final product using methods known in the art.

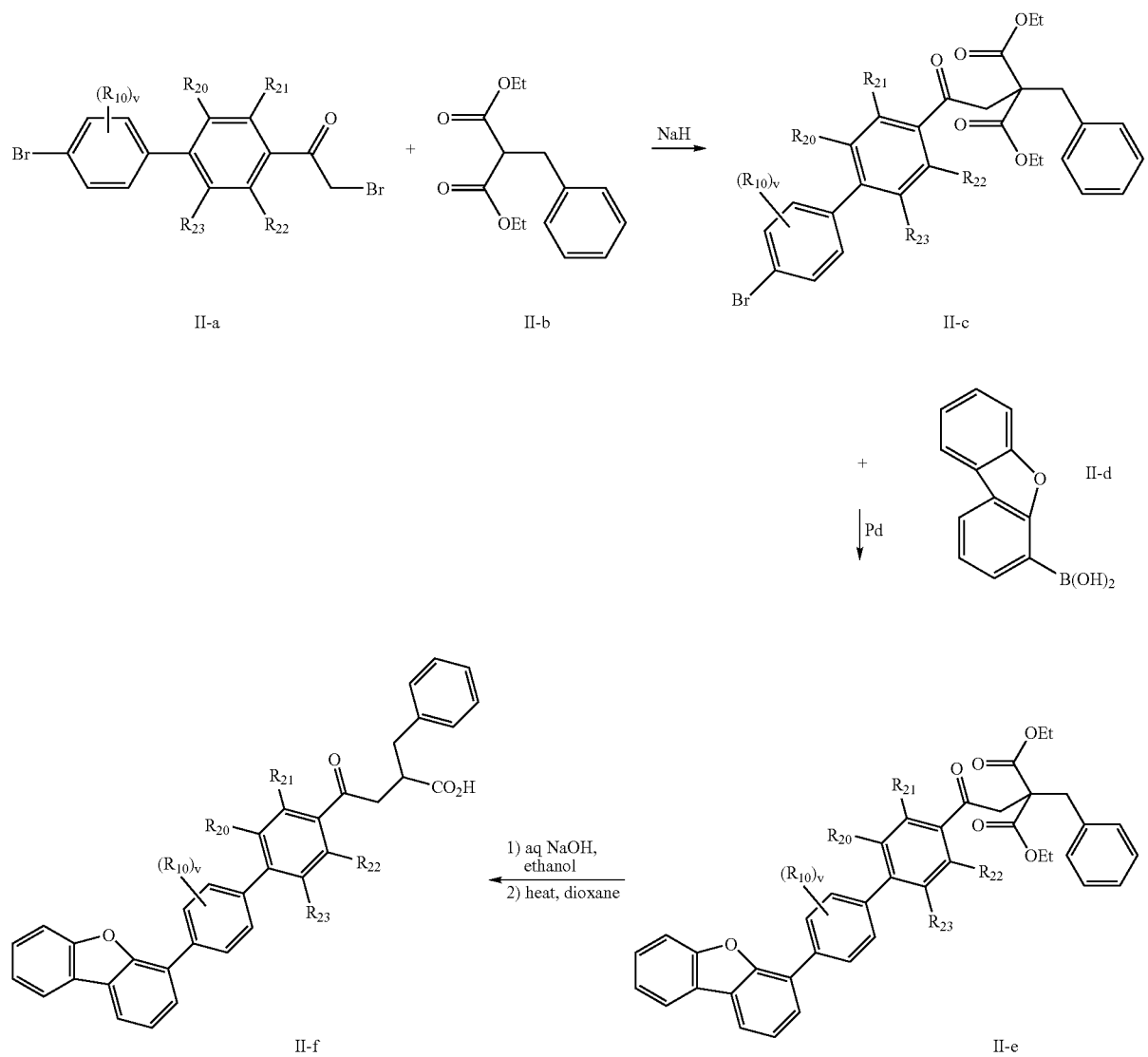

Those having skill in the art will recognize that the starting materials and reaction conditions may be varied, the sequence of the reactions altered, and additional steps employed to produce compounds encompassed by the present invention, as demonstrated by the following examples. In some cases, protection of certain reactive functionalities may be necessary to achieve some of the above transformations. In general, the need for such protecting groups as well as the conditions necessary to attach and remove such groups will be apparent to those skilled in the art of organic synthesis.

The disclosures of all articles and references mentioned in this application, including patents, are incorporated herein by reference.

The preparation of the compounds of the present invention is illustrated further by the following examples, which are not to be construed as limiting the invention in scope or spirit to the specific procedures and compounds described in them.

EXAMPLE 1

Preparation of 2-Benzyl-4-[4'-(2-benzyl-benzofuran-3-yl)-biphenyl-4-yl]-4-oxo-butyric acid

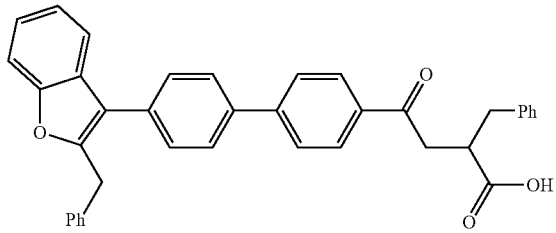

Step 1: Preparation of 5-[2-(4-Bromophenyl)-2-oxoethyl]-2,2-dimethyl-[1,3]dioxane-4,6-dione

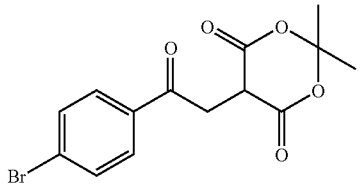

A solution of Meldrum's acid (5.0 g, 35 mmol) in anhyd THF (25 mL) was added cautiously to a stirred suspension of sodium hydride (95%, 960 mg, 38 mmol) in anhyd THF (25 mL). The resulting solution was stirred at room temperature for 1 h. A solution of 2,4'-dibromoacetophenone (11.6 g, 42 mmol) in anhyd THF (25 mL) was added dropwise, and the resultant solution was stirred at room temperature for 16-24 h (TLC control). The reaction mixture was poured into water (50 mL), acidified to pH 2-3 with 0.5 N hydrochloric acid and extracted with ethyl acetate (3×50 mL). The combined extract was washed with water, sat'd aq NaCl, dried over anhyd $MgSO_4$, filtered and concentrated in vacuo. Trituration and filtration from MeOH afforded the title compound as a white solid (6.56 g).

Step 2: Preparation of 2-Benzyl-3-[4-(4,4,5,5-tetramethyl-[1,3,2]-dioxaborolan-2-yl)phenyl]-benzofuran

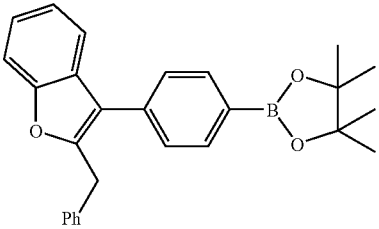

A solution of bis-(pinacolato)diboron (2.64 g, 10.41 mmol) in anhyd DMSO (20 mL) was added to a stirred suspension of trifluoromethanesulfonic acid-4-(2-benzyl-benzofuran-3 yl)phenyl ester, (4.09 g, 9.47 mmol) and potassium acetate (3.71 g, 37.9 mmol) in anhyd DMSO (20 mL). [1,1'-Bis(diphenylphosphino)-ferrocene]dichloropalladium(II)-DCM complex (770 mg, 0.95 mmol) was added as a solid, and the resulting suspension was heated to 80° C. for 4 h. The reaction mixture was cooled to room temperature, diluted with diethyl ether (150 mL), washed with water (2×50 mL), sat'd aq NaCl (3×50 mL), dried over anhyd $MgSO_4$, filtered and concentrated in vacuo. Purification of the product by flash column chromatography, using 10% ethyl acetate/hexane as eluent, afforded the title compound as a white solid (2.96 g).

Step 3: Preparation of 5-{2-[4'-(2-Benzylbenzofuran-3-yl)-biphen-4-yl]-2-oxoethyl}-2,2-dimethyl-[1,3]dioxane-4,6-dione

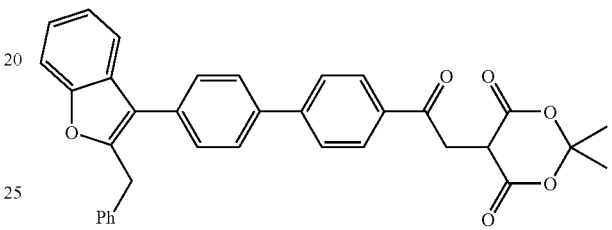

A solution of 2-benzyl-3-[4'-(4,4,5,5-tetramethyl-[1,3,2]-dioxaborolan-2-yl)phenyl]-benzofuran (500 mg, 1.22 mmol) in anhyd DMSO (5 mL) was added to a stirred suspension of 5-[2-(4-bromophenyl)-2-oxoethyl]-2,2-dimethyl-[1,3]dioxane-4,6-dione (436 mg, 1.22 mmol) and tripotassium phosphate (1.04 g, 4.88 mmol) in anhyd DMSO (5 mL). [1,1'-Bis(diphenylphosphino)ferrocene]dichloropalladium(II)-DCM complex (100 mg, 0.12 mmol) was added as a solid, and the resulting suspension was heated to 80° C. for 2 h. The reaction mixture was cooled to room temperature, diluted with diethyl ether (150 mL), washed with water (2×50 mL), sat'd aq NaCl (3×50 mL), dried over anhyd $MgSO_4$, filtered and concentrated in vacuo. Purification by flash column chromatography (50-60% ethyl acetate in heptane) afforded the title compound as an off-white solid (502 mg).

Step 4: Preparation of 5-Benzyl-5-{2-[4'-(2-benzylbenzofuran-3-yl)-biphen-4-yl]-2-oxoethyl}-2,2-dimethyl-[1,3]dioxane-4,6-dione

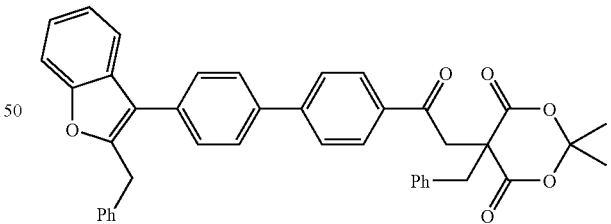

A solution of 5-{2-[4'-(2-benzylbenzofuran-3-yl)-biphen-4-yl]-2-oxoethyl}-2,2-dimethyl-[1,3]dioxane-4,6-dione (200 mg, 0.37 mmol) in THF/DMF (5:1; 6 mL) was added dropwise to a stirred suspension of sodium hydride (95%, 10.2 mg, 0.40 mmol) in anhyd THF (5 mL) at room temperature. The clear solution was stirred at room temperature for 30 min and then a solution of benzyl bromide (76 mg, 0.44 mmol) in THF (5 mL) was added dropwise, followed by the addition of tetra-n-butylammonium iodide (5 mg) as a solid. The reaction mixture was warmed to 60° C. for 4 h (TLC control), cooled to room temperature and then water (10 mL) was added cautiously. The reaction mixture was extracted with diethyl ether (3×15 mL). The combined organic extracts were washed successively with water (2×10 mL), sat'd aq NaCl (3×10 mL), dried over anhyd MgSO₄, filtered and concentrated in vacuo. Purification by trituration and filtration from MeOH afforded the title compound as a pale yellow solid (210 mg).

Step 5: Preparation of 2-Benzyl-4-[4'-(2-benzylbenzofuran-3-yl)biphen-4-yl]-4-oxobutyric acid

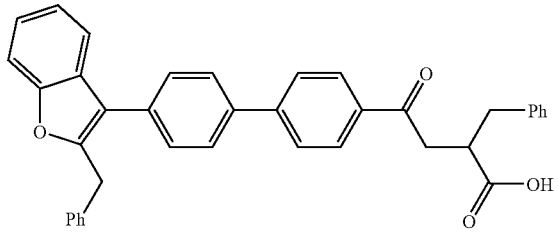

2 N Hydrochloric acid (1 mL) was added to a stirred solution of 5-benzyl-5-(2-[4'-(2-benzylbenzofuran-3-yl)-biphen-4-yl]-2-oxoethyl)-2,2-dimethyl-[1,3]dioxane-4,6-dione (200 mg) in THF (5 mL), and the resultant solution was heated at 70° C. for 6 h and then cooled to room temperature and concentrated in vacuo. The resulting solid was redissolved in DMSO (5 mL), and heated to 150° C. for 3 h before being cooled to room temperature, and diluted with water (20 mL), and extracted with ethyl acetate (3×20 mL). The combined extract was washed with water (2×10 mL), sat'd aq NaCl (3×10 mL), dried over anhyd MgSO₄, filtered and concentrated in vacuo. Purification by trituration and filtration from MeOH afforded the title compound as a pale yellow solid (65 mg).

EXAMPLE 2

Preparation of 4-(4'-Dibenzofuran-4-yl-biphenyl-4-yl)-4-oxo-2-(3-trifluoromethyl-benzyl)-butyric acid

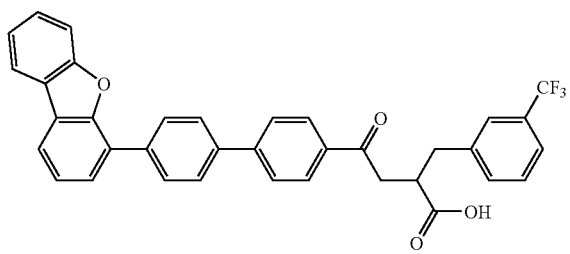

Step 1: Preparation of Diallyl-2-(3-trifluoromethylbenzyl) malonate

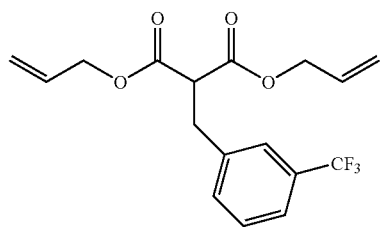

Diallyl malonate (1.2 g, 6.52 mmol) was added dropwise to a stirred suspension of sodium hydride (95%, 172 mg, 6.85 mmol) in anhyd THF (30 mL) at room temperature. The clear solution was stirred at room temperature for 30 min and then a solution of 3-trifluoromethylbenzyl bromide (1.7 g, 7.18 mmol) in THF (10 mL) was added dropwise. The reaction mixture was warmed to 50° C. for 4 h (TLC control), cooled to room temperature and then water (10 mL) was added cautiously. The reaction mixture was acidified to pH 3 with 2 N hydrochloric acid and then extracted with ethyl acetate (3×30 mL). The combined organic extracts were washed successively with water and sat'd aq NaCl, dried over anhyd MgSO₄, filtered and concentrated in vacuo. Purification by flash column chromatography (10% ethyl acetate in heptane) afforded the title compound as a colorless oil (1.03 g).

Step 2: Preparation of Diallyl-2-[2-(4-bromophenyl)-2-oxoethyl]-2-(3-trifluoromethylbenzyl)malonate

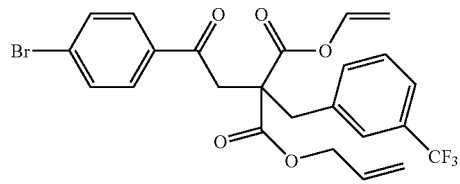

Diallyl-2-(3-trifluoromethylbenzyl)malonate (1.03 g, 3.01 mmol) in anhyd THF (20 mL) was added dropwise to a stirred suspension of sodium hydride (95%, 84 mg, 3.31 mmol) in anhyd THF (20 mL) at room temperature. The clear solution was stirred at room temperature for 30 min and then a solution of 2,4'-dibromoacetophenone (1.0 g, 3.61 mmol) in THF (10 mL) was added dropwise. The reaction mixture was warmed to 50° C. for 3 h (TLC control), cooled to room temperature and then water (10 mL) was added cautiously. The reaction mixture was acidified to pH 3 with 2 N hydrochloric acid and then extracted with ethyl acetate (3×30 mL). The combined extract was washed with water, sat'd aq NaCl, dried over anhyd MgSO₄, filtered and concentrated in vacuo. Purification by flash column chromatography (10% ethyl acetate in heptane) afforded the title compound as a colorless oil (1.23 g)

step 3: Preparation of Methyl-4-(4-bromophenyl)-4-oxo-2-(3-trifluoromethylbenzyl)butyrate.

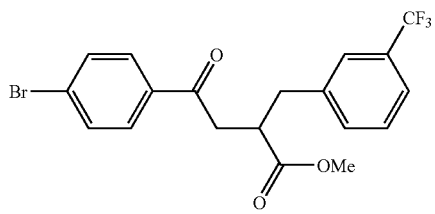

3 N Sodium hydroxide (3 mL) was added dropwise to a stirred solution of diallyl-2-[2-(4-bromophenyl)-2-oxoethyl]-2-(3-trifluoromethylbenzyl)malonate in THF (20 mL) and MeOH (3 mL), and the reaction was stirred at room temperature until complete (TLC control). The reaction mixture was washed with diethyl ether (2×10 mL), then acidified to pH 2 with 6 N hydrochloric acid and extracted with ethyl acetate (3×20 mL). The combined organic extracts were washed with water, sat'd aq NaCl, dried over anhyd MgSO₄, filtered and concentrated in vacuo to yield 2-[2-(bromophenyl)-2-oxoethyl]-2-(3-trifluoromethyl-benzyl)malonic acid as a pale yellow solid, which was used immediately without further purification.

The crude malonic acid was redissolved in dioxane (25 mL). 6 N Hydrochloric acid (3 drops) was added and then the solution was heated to reflux for 16 h, and then cooled to room temperature and diluted with ethyl acetate (50 mL). The organic phase was washed with water, sat'd aq NaCl, dried over anhyd MgSO₄, filtered and concentrated in vacuo to yield 4-(4-bromophenyl)-4-oxo-2-(3-trifluoromethylbenzyl)butyric acid as a white solid (790 mg), which was used without further purification.

The crude acid, from the previous step, was dissolved in anhyd MeOH (10 mL) and cooled to 0° C. Thionyl chloride (340 mg, 220 µL, 2.85 mmol) was added dropwise. The reaction mixture was stirred at 0° C. for 30 min and then warmed to room temperature and stirred for 3 h. The reaction mixture was poured into ice water. A saturated solution of sodium hydrogen carbonate was added to adjust the pH to 8-9, and then the solution was extracted with diethyl ether (3×20 mL). The combined organic extracts were washed with water, sat'd aq NaCl, dried over anhyd MgSO₄, filtered and concentrated in vacuo. Purification by flash column chromatography (20% ethyl acetate in hexane) afforded the title compound as a colorless oil (640 mg).

Step 4: Preparation of Methyl-4-(4'-hydroxybiphen-4-yl)-4-oxo-2-(3-trifluoromethylbenzyl)butyrate.

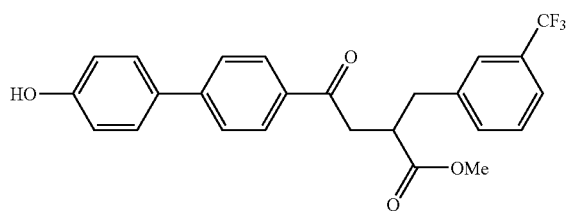

A solution of 4-hydroxyphenylboronic acid (160 mg, 1.2 mmol) in MeOH (3 mL) was added to a stirred solution of methyl-4-(4-bromophenyl)-4-oxo-2-(3-trifluoromethyl-benzyl)butyrate (270 mg, 0.6 mmol) in toluene (10 mL). Tetrakis-(Triphenylphosphine)-palladium(0) (21 mg, 4 mol %) and 2 N sodium carbonate (0.75 mL, 1.5 mmol) were added and then the reaction was heated to 90° C. (oil bath temp.) for 4-5 h until complete (TLC control). The reaction mixture was cooled to room temperature, acidified to pH 3 with 0.5 N hydrochloric acid and partitioned between water and ethyl acetate. The phases were separated, the aqueous phase being further extracted with ethyl acetate (2×20 mL). The combined organic extracts were washed with water and sat'd aq NaCl, dried over anhyd MgSO₄, filtered and concentrated. Trituration and filtration from MeOH afforded the title compound has a white solid (200 mg).

Step 5: Preparation of Methyl-4-oxo-4-(4'-trilfouormethanesulfonyloxy-biphen-4-yl)-2-(3-trifluoromethybenzyl)butyrate.

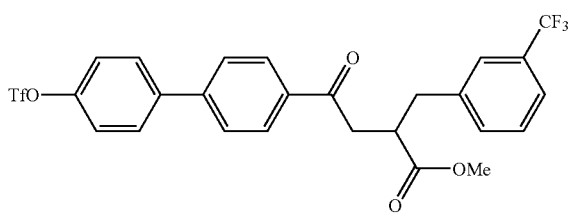

To a solution of Methyl-4-(4'-hydroxybiphen-4-yl)-4-oxo-2-(3-trifluoromethyl-benzyl)butyrate (200 mg, 0.45 mmol) in methylene chloride (6 mL) was added triethylamine (91 mg, 125 µL, 0.9 mmol), and 2-[N,N-bis(trifluoromethylsulfonyl)-amino]pyridine (179 mg, 0.48 mmol). The reaction mixture was stirred at room temperature for 2 h (TLC control), diluted with diethyl ether (30 mL), and washed with 1 N hydrochloric acid, water and sat'd aq NaCl, dried over anhyd MgSO₄, filtered and concentrated. Purification by flash column chromatography (20-30% ethyl acetate in heptane) afforded the title compound has a white solid (240 mg).

Step 6: Preparation of Methyl-4-(4'-dibenzofuran-4-ylbiphen-4-yl)-4-oxo-2-(3-trifluoromethy-benzyl)butyrate.

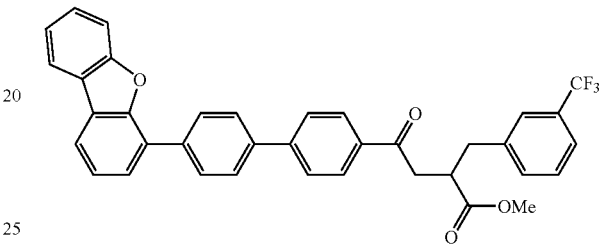

A solution of dibenzofuran-4-boronic acid (133 mg, 0.63 mmol) in methanol (5 mL) was added to a stirred solution of methyl-4-oxo-4-(4'-trilfouormethanesulfonyloxy-biphen-4-yl)-2-(3-trifluoromethy-benzyl)butyrate (240 mg, 0.42 mmol) and tetrakis(triphenylphosphine)-palladium(0) (25 mg, 5 mol %) in toluene (20 mL). 2 N sodium carbonate (0.5 mL, 1.0 mmol) was added and then the reaction was heated to 90° C. (oil bath temp.) for 2-3 h until complete (TLC control).

The reaction mixture was cooled to room temperature and partitioned between water and ethyl acetate. The phases were separated, the aqueous phase being further extracted with ethyl acetate (2×20 mL). The combined extract was washed with water and sat'd aq NaCl. The organic solution was dried over anhyd MgSO₄, filtered and concentrated in vacuo. Purification by flash column chromatography (20-30% ethyl acetate in heptane) afforded the title compound has a white solid (230 mg).

Step 7: Preparation of 4-(4'-Dibenzofuran-4-ylbiphen-4-yl)-4-oxo-2-(3-trifluoromethybenzyl)butyric acid.

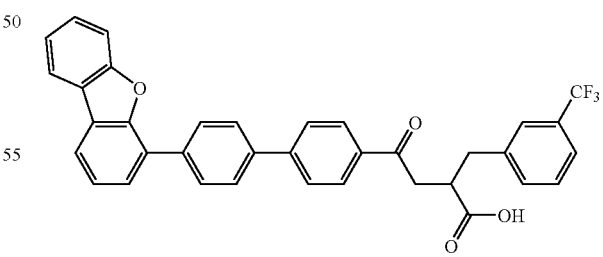

2 N Sodium hydroxide solution (1 mL) was added dropwise to a stirred solution of methyl-4-(4'-dibenzofuran-4-ylbiphen-4-yl)-4-oxo-2-(3-trifluoromethy-benzyl)butyrate (220 mg) in tetrahydrofuran (5 mL) and methanol (2 mL). The clear reaction mixture was stirred at room temperature until the reaction was complete (TLC control), and then diluted with water (5 mL), and acidified to pH 3 with 2N hydrochloric acid. The reaction mixture was extracted with ethyl acetate (2×20 mL). The combined organic extracts were washed with water, sat'd aq NaCl, dried over anhyd MgSO₄, filtered and concentrated in vacuo. Purification by flash column chromatography (5-10% methanol in methylene chloride) afforded the title compound has a white solid (190 mg). Rf: 0.60 (10% methanol in dichloromethane); 1H-NMR (CDCl₃, 300 MHz): δ 8.06 (4H, m, Ar—H), 7.96 (2H, m, Ar—H), 7.77 (4H, t, J=9 Hz, Ar—H), 7.62 (2H, t, J=9 Hz, Ar—H), 7.47 (6H, m, Ar—H), 7.37 (1H, t, J=8 Hz, Ar—H), 3.46 (2H, m), 3.26 (1H, dd, J=16, 7 Hz), 3.12 (1H, m), 3.02 (1H, dd, J=16, 8 Hz); ESI-LCMS e/z calcd for C₃₆H₂₅F₃O₄:578.583, found 579 (M+H)⁺, 601 (M+Na)⁺.

EXAMPLE 3

The following compounds were prepared essentially according to the methods and procedures described above in the schemes and examples 1 and 2.

In another aspect, the invention provides a compound according to formula 1 selected from the group consisting of ({4, -[3-(benzylamino)imidazo[1,2-a]pyridin-2-yl]biphenyl-4-yl}oxy)(phenyl)acetic acid;
{[4'-(5-methyl-1H-indol-1-yl)biphenyl-4-yl]oxy}(phenyl)acetic acid;
({4'-[3-(butylamino)imidazo[1,2-a]pyridin-2-yl]biphenyl-4-yl}oxy)(phenyl)acetic acid;
methyl ({4'-[(2-benzoylphenoxy)methyl]biphenyl-4-yl}oxy)(phenyl)acetate;
methyl ({4'-[(2-benzylphenoxy)methyl]biphenyl-4-yl}oxy)(phenyl)acetate;
methyl ({4'-[(9H-fluoren-2-yloxy)methyl]biphenyl-4-yl}oxy)(phenyl)acetate;
methyl ({4'-[(3-benzoylphenoxy)methyl]biphenyl-4-yl}oxy)(phenyl)acetate;
({4'-[(3-benzoylphenoxy)methyl]-biphenyl-4-yl}oxy)(phenyl)acetic acid;
({4-[(2-benzoylphenoxy)methyl]biphenyl-4-yl}oxy)(phenyl)acetic acid;
2-{[4'-(2-benzyl-1-benzofuran-3-yl)biphenyl-4-yl]oxy}-3-phenylpropanoic acid;
{[4-(1-butylindolizin-2-yl)biphenyl-4-yl]oxy}(phenyl)acetic acid;
[4-(1-benzyl-1H-indol-6-yl)phenoxy](phenyl)acetic acid;
({4'-[10-(ethoxycarbonyl)pyrido[1,2-a]indol-3-yl]biphenyl-4-yl}oxy)(phenyl)acetic acid;
{[4-(1-benzofuran-2-yl)biphenyl-4-yl]oxy}(phenyl)acetic acid;
{[4'-(1H-indol-1-yl)biphenyl-4-yl]oxy}(phenyl)acetic acid;
methyl {[4'-(1-benzyl-1H-indol-6-yl)biphenyl-4-yl]oxy}(phenyl)acetate;
4-(4'-Dibenzofuran-4-yl-biphenyl-4-yl)-4-oxo-2-(3-trifluoromethyl-benzyl)-butyric acid;
{[4-(1-benzyl-1H-indol-6-yl)biphenyl-4-yl]oxy}(phenyl)acetic acid;
{[4'-(1-benzyl-1H-indol-5-yl)biphenyl-4-yl]oxy}(phenyl)acetic acid;
2-{[4'-(1-butylindolizin-2-yl)biphenyl-4-yl]oxy}propanoic acid;
N-{[4'-(1-butylindolizin-2-yl)biphenyl-4-yl]sulfonyl}phenylalanine;
N-{[4'-(2-benzyl-1-benzofuran-3-yl)biphenyl-4-yl]sulfonyl}phenylalanine;
N-benzyl-N-{[4'-(2-benzyl-1-benzofuran-3-yl)biphenyl-4-yl]sulfonyl}glycine;
({[4'-(2-benzyl-1-benzofuran-3-yl)biphenyl-4-yl]sulfonyl}amino)(phenyl)acetic acid;
(2R)-2-{[4'-(1-butylindolizin-2-yl)biphenyl-4-yl]oxy}-3-phenylpropanoic acid;
4-(4-Dibenzofuran-4-yl-phenyl)-4-oxo-2-(3-trifluoromethyl-benzyl)-butyric acid;
(2S)-2-{[4'-(1-butylindolizin-2-yl)biphenyl-4-yl]oxy}-4-phenylbutanoic acid;
({4'-[(2-butyl-1-benzofuran-3-yl)methyl]biphenyl-4-yl}oxy)(phenyl)acetic acid;
ethyl N-{[4'-(2-benzyl-1-benzofuran-3-yl)biphenyl-4-yl]sulfonyl}-N-methylphenylalaninate;
N-{[4'-(2-benzyl-1-benzofuran-3-yl)biphenyl-4-yl]sulfonyl}-N-methylphenylalanine;
ethyl N-{[4'-(1-butylindolizin-2-yl)biphenyl-4-yl]carbonyl}phenylalaninate;
N-{[4'-(1-butylindolizin-2-yl)biphenyl-4-yl]carbonyl}phenylalanine;
{[2"-(1,3-benzoxazol-2-yl)-1,1':4',1"-terphenyl-4-yl]oxy}(phenyl)acetic acid;
({4'-[(2-butyl-1-benzofuran-3-yl)carbonyl]biphenyl-4-yl}oxy)(phenyl)acetic acid;
methyl {[4'-(1-butylindolizin-2-yl)biphenyl-4-yl]sulfonyl}(phenyl)acetate;
N-{[4'-(2-benzyl-1-benzofuran-3-yl)biphenyl-4-yl]carbonyl}phenylalanine;
N-{[4-(2-benzyl-1-benzofuran-3-yl)biphenyl-4-yl]carbonyl}-N-methylphenylalanine;
{[4'-(1-butylindolizin-2-yl)biphenyl-4-yl]sulfonyl}(phenyl)acetic acid;
({[4'-(2-benzyl-1-benzofuran-3-yl)biphenyl-4-yl]carbonyl}amino)(phenyl)acetic acid;
2-{[41-(2-benzyl-1-benzofuran-3-yl)biphenyl-4-yl]oxy}propanoic acid;
{[4-(1-butylindolizin-2-yl)biphenyl-4-yl]amino}(phenyl)acetic acid;
N-({4'-[(2-butyl-1-benzofuran-3-yl]methyl]biphenyl-4-yl)sulfonyl)-N-methylphenylalanine;
N-({4'-[(2-butyl-1-benzofuran-3-yl)methyl]biphenyl-4-yl}carbonyl)-N-methylphenylalanine;
N-{[4-(2-benzyl-1-benzofuran-3-yl)biphenyl-4-yl]carbonyl}-N-methylvaline;
2-benzyl-4-[4'-(2-benzyl-1-benzofuran-3-yl)biphenyl-4-yl]-4-oxobutanoic acid;
N-[4'-(2-benzyl-1-benzofuran-3-yl)-3-nitrobiphenyl-4-yl]phenylalanine;
N-[4'-(2-benzyl-1-benzofuran-3-yl)-3-nitrobiphenyl-4-yl]-N-methyl-L-phenylalanine;
N-[4'-(2-benzyl-1-benzofuran-3-yl)-3-nitrobiphenyl-4-yl]-N-methyl-D-phenylalanine;
N-{[4'-(2-benzyl-1-benzofuran-3-yl)-3-fluorobiphenyl-4-yl]sulfonyl}phenylalanine;
{[4-(1-benzothien-2-yl)biphenyl-4-yl]oxy}(phenyl)acetic acid;
N-[4-(2-benzyl-1-benzofuran-3-yl)-3-nitrobiphenyl-4-yl]-N-(4-nitrobenzoyl)-L-phenylalanine;
[(4'-dibenzo[b,d]furan-4-ylbiphenyl-4-yl)oxy](phenyl)acetic acid;
N-{[4'-(2-benzyl-1-benzofuran-3-yl)-3-fluorobiphenyl-4-yl]sulfonyl}-N-methylphenylalanine;
[(4-1-butyl-1,1:4',1"-terphenyl-4-yl)oxy](phenyl)acetic acid;
N²-[4'-(2-benzyl-1-benzofuran-3-yl)-3-nitrobiphenyl-4-yl]glutamine;
4-[4'-(2-benzyl-1-benzofuran-3-yl)biphenyl-4-yl]-2-[2-(1,3-dioxo-1,3-dihydro-2H-isoindol-2-yl)ethyl]-4-oxobutanoic acid;
({4'-[(2-benzyl-7-fluoro-1-benzofuran-3-yl)carbonyl]biphenyl-4-yl}oxy)(phenyl)acetic acid;

N-[4'-(2-benzyl-1-benzofuran-3-yl)-3-nitrobiphenyl-4-yl]
methionine;
N-[4'-(2-benzyl-1-benzofuran-3-yl)-3-nitrobiphenyl-4-yl]
serine;
N-[4'-(2-benzyl-1-benzofuran-3-yl)-3-nitrobiphenyl-4-yl]
alanine;
N-{4'-[(2-benzyl-7-ethoxy-1-benzofuran-4-yl)methyl]-3-nitrobiphenyl-4-yl}phenylalanine;
N-[4'-(2-benzyl-4-fluoro-1-benzofuran-3-yl)-3-nitrobiphenyl-4-yl]phenylalanine;
2-benzyl-4-[4'-(2-benzyl-1-benzofuran-3-yl)-3,5-dimethylbiphenyl-4-yl]-4-oxobutanoic acid;
2-benzyl-4-[4'-(2-benzyl-1-benzofuran-3-yl)biphenyl-3-yl]-4-oxobutanoic acid;
2-benzyl-4-[4'-(2-benzyl-1-benzofuran-3-yl)biphenyl-2-yl]-4-oxobutanoic acid;
N-{4'-(2-benzyl-1-benzofuran-3-yl)-3-[(phenylacetyl)amino]biphenyl-4-yl}phenylalanine;
4-[4'-(2-benzyl-1-benzofuran-3-yl)biphenyl-4-yl]-2-[4-(methylsulfonyl)benzyl]-4-oxobutanoic acid;
N-{[4'-(2-benzyl-1-benzofuran-3-yl)biphenyl-4-yl]sulfonyl}-4-fluorophenylalanine;
N-{[4'-(2-benzyl-1-benzofuran-3-yl)biphenyl-4-yl]sulfonyl}-4-fluoro-N-methylphenylalanine;
N-{[4'-(2-benzyl-1-benzofuran-3-yl)biphenyl-4-yl]sulfonyl}-3-fluorophenylalanine;
N-{[4'-(2-benzyl-1-benzofuran-3-yl)biphenyl-4-yl]sulfonyl}-3-fluoro-N-methylphenylalanine;
N-{[4'-(2-benzyl-1-benzofuran-3-yl)biphenyl-4-yl]sulfonyl}-N-ethyl-4-fluorophenylalanine;
N-{[4'-(2-benzyl-1-benzofuran-3-yl)biphenyl-4-yl]sulfonyl}leucine;
N-{[4'-(2-benzyl-1-benzofuran-3-yl)biphenyl-4-yl]sulfonyl}alanine;
2-({[4'-(2-benzyl-1-benzofuran-3-yl)biphenyl-4-yl]sulfonyl}amino)butanoic acid;
N-{[4'-(2-benzyl-1-benzofuran-3-yl)biphenyl-4-yl]sulfonyl}-N-[3-(trifluoromethyl)benzyl]leucine;
2-{{[4'-(2-benzyl-1-benzofuran-3-yl)biphenyl-4-yl]sulfonyl}[3-(trifluoromethyl)benzyl]amino}butanoic acid;
methyl 4-(4'-dibenzo[b,d]furan-4-ylbiphenyl-4-yl)-4-oxo-2-[3-(trifluoromethyl)benzyl]butanoate;
[(4-{[(9-oxo-9H-fluoren-1-yl)oxy]methyl}biphenyl-4-yl)oxy](phenyl)acetic acid;
methyl {[4'-(1-benzofuran-2-yl)biphenyl-4-yl]oxy}(phenyl)acetate;
({4'-[3-(butylamino)imidazo[1,2-a]pyridin-2-yl]biphenyl-4-yl}amino)(phenyl)acetic acid;
{[4-(1-benzothien-3-yl)biphenyl-4-yl]oxy}(phenyl)acetic acid;
methyl {[4'-(1-benzyl-1H-indol-5-yl)biphenyl-4-yl]oxy}(phenyl)acetate;
ethyl ({[4'-(2-benzyl-1-benzofuran-3-yl)biphenyl-4-yl]sulfonyl}amino)(phenyl)acetate;
methyl 2-(4-benzo[b]naphtho[2,3-d]furan-11-ylphenoxy)propanoate;
3-({[4'-(2-benzyl-1-benzofuran-3-yl)biphenyl-4-yl]carbonyl}amino)butanoic acid;
N-{[4'-(5-methyl-1H-indol-1-yl)biphenyl-4-yl]carbonyl}phenylalanine;
N-{[4'-(1H-indol-1-yl)biphenyl-4-yl]carbonyl}-L-phenylalanine;
N-(3'-fluoro-3-nitro-1,1':4',1''-terphenyl-4-yl)phenylalanine;
2-benzyl-4-[4'-(1H-indol-1-yl)biphenyl-4-yl]-4-oxobutanoic acid;
2-[4'-(2-Benzyl-benzofuran-3-yl)-3-nitro-biphenyl-4-ylamino]-3-phenyl-propionic acid;
4-(4'-dibenzo[b,d]furan-4-ylbiphenyl-4-yl)-4-oxo-2-[3-(trifluoromethyl)benzyl]butanoic acid;
[(4'-dibenzo[b,d]thien-4-ylbiphenyl-4-yl)oxy](phenyl)acetic acid;
(4'-Dibenzofuran-4-yl-biphenyl-4-ylmethoxyimino)-phenyl-acetic acid;
3-(4'-Dibenzofuran-4-yl-biphenyl-4-ylmethoxyimino)-3-phenyl-propionic acid;
[4'-(5-Chloro-indol-1-yl)-biphenyl-4-yloxy]-phenyl-acetic acid;
(3-Chloro-4'-dibenzofuran-4-yl-biphenyl-4-yloxy)-phenyl-acetic acid;
(4'-Dibenzofuran-4-yl-2-methyl-biphenyl-4-yloxy)-phenyl-acetic acid;
(4'-Dibenzofuran-4-yl-3-fluoro-biphenyl-4-yloxy)-phenyl-acetic acid;
(2-Chloro-4'-dibenzofuran-4-yl-biphenyl-4-yloxy)-phenyl-acetic acid; and
(4'-Dibenzofuran-4-yl-2-trifluoromethyl-biphenyl-4-yloxy)-phenyl-acetic acid.

In still another aspect, the invention provides compounds of formula 1 selected from

| | |
|---|---|
| 2-[4'-(2-Benzyl-benzofuran-3-yl)-3-fluoro-biphenyl-4-sulfonylamino]-3-phenyl-propionic acid; | Isolated as an off-white solid. $R_f$ 0.32 (10% Methanol-90% Methylene Chloride); $^1$H NMR(CDCl$_3$) 12.8(br. s, 1H), 8.57(br. s, 1H), 7.93-7.16(m, 21H), 4.29(s, 2H), 3.97(m, 1H); 3.02-2.75(m, 2H); LCMS m/z calcd for $C_{36}H_{28}FNO_5$S: 605.68 found 604.0(M+1). |
| 2-{[4'-(2-Benzyl-benzofuran-3-yl)-3-fluoro-biphenyl-4-sulfonyl]-methyl-amino}-3-phenyl-propionic acid; | Isolated as an off white solid. $R_f$ 0.36 (10% Methanol-90% Methylene Chloride); $^1$H NMR(CDCl$_3$) 7.79(tr, J=7.8Hz, 1H), 7.69-7.61(m, 4H), 7.49(d, J=7.2Hz, 1H), 7.42(d, J=8.4Hz, 1H), 7.32-7.12(14H), 4.94(q, J=5.1Hz, 1H), 4.26(s, 2H), 3.32(dd, J=14.4, 5.7Hz, 1H), 3.07(3H), 3.07-2.92(1H). |
| 4-[4'-(2-Benzyl-benzofuran-3-yl)-biphenyl-4-yl]-2-[2-(1,3-dioxo-1,3-dihydro-isoindol-2-yl)-ethyl]-4-oxo-butyric acid; | Isolated as a beige foam. $R_f$ 0.39(10% Methanol-90% Methylene Chloride); $^1$H NMR (CDCl$_3$) 8.05(d, J=8.1Hz, 2H), 7.82-7.23(m, 19H), 4.24(s, 2H), 3.86(br s, 2H), 3.60(dd, J=18.0, 7.6Hz, 1H), 3.29-3.13(m, 2H), 2.20(m, 1H), 2.01(m, 1H); LCMS m/z calcd for $C_{41}H_{31}NO_6$: 633.69 found 634.0(M+1). |

-continued

| | |
|---|---|
| 2-Benzyl-4-[4'-(2-benzyl-benzofuran-3-yl)-3,5-dimethyl-biphenyl-4-yl]-4-oxo-butyric acid; | Light yellow solid. $R_f$ 0.43(10% Methanol-90% Methylene Chloride); $^1$H NMR (DMSO-d6) 7.79(d, J=8.1Hz, 2H), 7.62-7.16(m, 18H), 4.26(s, 2H), 3.11-2.76(m, 5H), 2.13(s, 6H); LCMS m/z calcd for $C_{40}H_{34}O_4$: 578.7 found 579.0(M+1). |
| 2-Benzyl-4-(4'-indol-1-yl-biphenyl-4-yl)-4-oxo-butyric acid; | Isolated as a white solid. $R_f$ 0.44 (10% Methanol-90% Methylene Chloride); $^1$H NMR(DMSO-d6) 12.2(br. s, 1H), 8.03-7.62(m, 11H), 7.29-7.13(m, 7H), 6.72(br s, 1H), 3.46-3.37(m, 1H), 3.16-2.81(m, 4H); LCMS m/z calcd for $C_{31}H_{25}NO_3$: 459.5 found 460.3(M+1). |
| 2-Benzyl-4-[4'-(2-benzyl-benzofuran-3-yl)-biphenyl-3-yl]-4-oxo-butyric acid; | Isolated as a light yellow foam. $R_f$ 0.33(10% Methanol-90% Methylene Chloride); $^1$H NMR(DMSO-d6) 8.21(s, 8.21, 1H), 8.00-7.87(m, 4H), 7.68-7.56(m, 5H), 7.35-7.15(m, 12H), 4.28(s, 2H), 3.53-3.44(m, 1H), 3.18-2.80(m, 4H); LCMS m/z calcd for $C_{38}H_{30}O_4$: 550.6 found 551.3(M+1). |
| 2-Benzyl-4-[4'-(2-benzyl-benzofuran-3-yl)-biphenyl-2-yl]-4-oxo-butyric acid; | Isolated as a yellow foam. $R_f$ 0.35(10% Methanol-90% Methylene Chloride); $^1$H NMR (CDCl$_3$) 6.94-7.69(m, 22H), 4.25(s, 2H), 3.12-3.05(m, 1H), 2.90-2.74(m, 2H), 2.56(dd, $J_1$=13.5Hz, $J_2$=8.2Hz, 1H), 2.49(dd,, $J_1$=18.0Hz, $J_2$=4.6Hz, 1H); LCMS m/z calcd for $C_{38}H_{30}O_4$: 550.6 found 551.3(M+1). |
| 4-[4'-(2-Benzyl-benzofuran-3-yl)-biphenyl-4-yl]-2-(4-methanesulfonyl-benzyl)-4-oxo-butyric acid; | Isolated as a dark yellow solid., $R_f$ 0.41(10% Methanol-90% Methylene Chloride); $^1$H NMR(CDCl$_3$) 8.02(d, J=8.4Hz, 2H), 7.89(d, J=8.1Hz, 2H), 7.74(d, J=10.5Hz, 4H), 7.63(d, J=7.5Hz, 3H), 7.48(d, J=5.1Hz, 3H), 7.36-7.20(m, 7H), 4.26(s, 2H), 3.48(m, 3H), 3.30-3.00(m, 2H), 3.07(s, 3H). |
| 2-[4'-(2-Benzyl-benzofuran-3-yl)-biphenyl-4-sulfonylamino]-3-(4-fluoro-phenyl)-propionic acid; | Isolated as a white foam. $R_f$ 0.41(20% Methanol-80% Ethyl Acetate); $^1$H NMR(CDCl$_3$) 7.74-7.56(m, 9H), 7.42(d, J=7.8Hz, 1H), 7.29-7.14(m, 7H), 7.05(dd, $J_1$=8.6Hz, $J_2$=5.6Hz, 2H), 6.84(t, J=8.6Hz, 2H), 4.28(s, 2H), 4.10-4.03(s, 1H), 3.08(dd, $J_1$=5.0Hz, $J_2$=13.5Hz, 1H), 2.91(dd, $J_1$=14.0Hz, $J_2$=6.8Hz, 1H). |
| 2-{[4'-(2-Benzyl-benzofuran-3-yl)-biphenyl-4-sulfonyl]-methyl-amino}-3-(4-fluoro-phenyl)-propionic acid; | Isolated as an off-white solid. $R_f$ 0.52 (20% Methanol-80% Methylene Chloride); $^1$H NMR(DMSO-d$_6$) 8.35(br s, 1H), 7.82-6.90(m, 20H), 4.26(s, 2H), 3.93(m, 1H), 2.97(m, 1H), 2.72(m, 1H), 2.47(s, 3H). |
| 2-[4'-(2-Benzyl-benzofuran-3-yl)-biphenyl-4-sulfonylamino]-3-(3-fluoro-phenyl)-propionic acid; | Isolated as a white solid. $R_f$ 0.42 (20% Methanol-80% Ethyl Acetate); $^1$H NMR (DMSO-d$_6$) 8.66(d, J=9.3Hz, 1H), 7.94(d, J=8.0Hz, 2H), 7.90(d, J=8.4Hz, 2H), 7.80-7.66(m, 6H), 7.46-7.28(m, 8H), 7.07(d, J=8.4Hz, 2H), 4.38(s, 2H), 4.14(m, 1H), 3.08($J_1$=13.7Hz, $J_2$=5.3Hz, 1H), 2.93-2.85(m, 1H). |
| 2-{[4'-(2-Benzyl-benzofuran-3-yl)-biphenyl-4-sulfonyl]-methyl-amino}-3-(3-fluoro-phenyl)-propionic acid; | Isolated as an off-white solid. $R_f$ 0.20 (10% Methanol-90% Methylene Chloride); $^1$H NMR(DMSO-d$_6$) 7.88(d, J=8.4Hz, 2H), 7.80(d, J=8.4Hz, 2H), 7.71-7.53(m, 6H), 7.36-7.20(8H), 7.09-6.98(m, 3H), 4.83(dd, $J_1$=10.8Hz, $J_2$=4.8Hz, 1H), 4.29(s, 2H), 3.19(dd, $J_1$=14.1Hz, $J_2$=5.1Hz, 1H), 2.95(dd, $J_1$=14.7Hz, $J_2$=10.8Hz, 1H), 2.82(s, 3H). |
| 2-{[4'-(2-Benzyl-benzofuran-3-yl)-biphenyl-4-sulfonyl]-ethyl-amino}-3-(4-fluoro-phenyl)-propionic acid; | Isolated as a white solid. $R_f$ 0.38(10% Methanol-90% Methylene Chloride); $^1$H NMR (DMSO-d$_6$) 7.94-7.54(m, 10H), 7.38-7.00(m, 11H), 4.69(s, 2H), 3.33(m, integration for 2H obscured by $H_2O$), 2.93(m, 1H), 1.07(t, J=9Hz, 3H). |

| | |
|---|---|
| 2-[4'-(2-Benzyl-benzofuran-3-yl)-biphenyl-4-sulfonylamino]-4-methyl-pentanoic acid; | Isolated as an off-white foam. $R_f$ 0.24 (10% Methanol-90% Methylene Chloride); $^1$H NMR(DMSO-$d_6$) 12.61(br s, 1H), 8.22(d, J=8.4Hz, 1H), 7.92-7.56(10H), 7.34-7.25(m, 7H), 4.28(s, 2H), 3.68(m, 1H), 1.59-1.24(m, 3H), 0.82(d, J=6.3Hz, 3H), 0.70(d, J=6.6Hz, 3H). |
| 2-[4'-(2-Benzyl-benzofuran-3-yl)-biphenyl-4-sulfonylamino]-propionic acid; | Isolated as a beige foam. $R_f$ 0.43(20% Methanol-80% Methylene Chloride); $^1$H NMR (DMSO-$d_6$) 7.92-7.56(m, 10H), 7.31-7.23(m, 7H), 4.28(s, 2H), 3.65(m, 1H), 1.20(d, J=6.6Hz, 3H). |
| 2-[4'-(2-Benzyl-benzofuran-3-yl)-biphenyl-4-sulfonylamino]-butyric acid; | Isolated as a white solid. $R_f$ 0.20(10% Methanol-90% Methylene Chloride); $^1$H NMR (DMSO-$d_6$) 12.6(br s, 1H), 8.18(d, J=8.4Hz, 1H), 7.95-7.84(m, 7H), 7.70-7.56(m, 3H), 7.34-7.23(m, 7H), 4.29(s, 2H), 3.66(m, 1H), 1.57(m, 2H), 0.79(d, J=7.2Hz, 3H). |
| 2-(4'-Dibenzofuran-4-yl-biphenyl-4-sulfonylamino)-3-phenyl-propionic acid; | Isolated as an off-white solid. $R_f$ 0.20 (10% Methanol-90% Methylene Chloride); $^1$H NMR(DMSO-$d_6$) 8.06(t, J=7.5HZ, 2H), 7.95(d, J=8.1Hz, 2H), 7.78(d, J=8.4Hz, 2H), 7.69-7.28(m, 9H), 7.05-7.04(m, 5H), 3.83(m, 1H), 2.87(dd, J$_1$=5.4Hz, J$_2$=13.8Hz, 1H), 2.64(dd, J$_1$=9.6Hz, J$_2$=13.8Hz, 1H); LCMS m/z calcd for $C_{33}H_{25}NO_5$ S 547.62 found 548.3(M+1). |
| (4'-Dibenzofuran-4-yl-biphenyl-4-sulfonylamino)-phenyl-acetic acid; | Isolated as a white solid. $R_f$ 0.47 (20% Methanol-80% Methylene Chloride); $^1$H NMR(DMSO-$d_6$) 12.98(br s, 1H), 8.79(d, J=9.0Hz, 1H), 8.18(t, J=7.2Hz, 2H), 8.04(d, J=8.4Hz, 2H), 7.90-7.73(m, 8H), 7.54-7.42(m, 3H), 7.28-7.21(m, 5H), 4.95(d, J=9.3Hz, 1H). |
| 1-{4-[4-(4-Chloro-phenyl)-5-(4-ethyl-phenyl)-thiazol-2-ylcarbamoyl]-benzenesulfonyl}-pyrrolidine-2-carboxylic acid; | $R_f$ 0.08(20% methanol in dichloromethane) | and pharmaceutically acceptable salts thereof.

EXAMPLE 4

Method for Measuring PTP-1B Activity

The test compounds are evaluated for their in vitro inhibitory activity against recombinant human PTP1B with phosphotyrosyl dodecapeptide TRDI(P)YETD(P)Y(P)YRK [SEQ ID NO:1]. This corresponds to the 1142-1153 insulin receptor kinase regulatory domain, phosphorylated on the 1146, 1150 and 1151 tyrosine residues; IR-triphosphopeptide as a source of substrate. Enzyme reaction progression is monitored via the release of inorganic phosphate as detected by the malachite green-ammonium molybdate method for the phosphopeptide.

Preferred compounds of the invention exhibit $IC_{50}$ values of less than 10 μM; more preferred compounds of the invention exhibit $IC_{50}$ values of less than 1 μM. Particularly preferred compounds exhibit $IC_{50}$ values of less than 300 nM.

The invention and the manner and process of making and using it, are now described in such full, clear, concise and exact terms as to enable any person skilled in the art to which it pertains, to make and use the same. It is to be understood that the foregoing describes preferred embodiments of the invention and that modifications may be made therein without departing from the spirit or scope of the invention as set forth in the claims. To particularly point out and distinctly claim the subject matter regarded as invention, the following claims conclude this specification.

What is claimed is:

1. A compound of the formula:

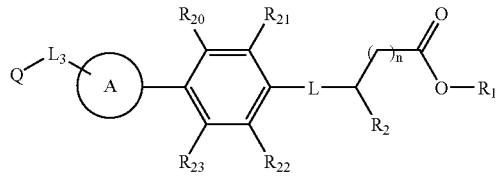

or a pharmaceutically acceptable salt thereof, wherein n is 0, 1, 2, 3, or 4;

$R_1$ is H, $C_1$-$C_6$ alkyl, phenyl($C_1$-$C_6$)alkyl, or $C_3$-$C_6$ alkenyl;

$R_2$ is phenyl, phenyl($C_1$-$C_4$) alkyl, $C_1$-$C_6$ alkyl, —($C_1$-$C_4$) alkyl-C(O)NH$_2$, —($C_1$-$C_4$) alkyl-C(O)NH($C_1$-$C_4$) alkyl, —($C_1$-$C_4$) alkyl-C(O)N($C_1$-$C_4$)alkyl($C_1$-$C_4$) alkyl, —($C_1$-$C_4$) alkyl-S(O)$_b$—($C_1$-$C_4$) alkyl, ($C_1$-$C_4$) hydroxyalkyl, —($C_1$-$C_4$) alkyl-phthalimidyl, —($C_1$-$C_4$) alkyl-piperidinyl, —($C_1$-$C_4$) alkyl-pyrrolidinyl, —($C_1$-$C_4$) alkyl-morpholinyl, wherein the phthalimidyl, piperidinyl, pyrrolidinyl, or morpholinyl groups are optionally fused to a phenyl ring and wherein said phthalimidyl, piperidinyl, pyrrolidinyl, or morpholinyl groups are, the phenyl portion, or both are optionally substituted with a total of 1, 2, 3, or 4 groups that are independently halogen, $C_1$-$C_4$ alkyl, $C_1$-$C_4$ alkoxy, —SO$_2$—($C_1$-$C_4$) alkyl ($C_1$-$C_4$) haloalkyl, or ($C_1$-$C_4$) haloalkoxy;

wherein b is 0, 1, or 2;

$R_{20}$, $R_{21}$, $R_{22}$, and $R_{23}$ are independently H, arylalkoxy, arylalkyl, halogen, alkyl, haloalkyl, OH, alkoxy, NO$_2$, NH$_2$, NH($C_1$-$C_6$)alkyl, N($C_1$-$C_6$ alkyl)($C_1$-$C_6$ alkyl), NH-aryl, NHC(O)—($C_1$-$C_4$ alkyl)-aryl, N($C_1$-$C_4$ alkyl) C(O)—($C_1$-$C_4$)alkyl-aryl, N($C_1$-$C_4$) alkyl-aryl, —NHSO$_2$-aryl, or —N($C_1$-$C_4$alkyl) SO$_2$aryl, wherein each of the above aryl groups are optionally substituted with 1, 2, 3, or 4 groups that are independently $C_1$-$C_6$ alkyl, $C_1$-$C_6$ alkoxy, halogen, OH, NO$_2$, haloalkyl, haloalkoxy;

L is O;

$L_3$ is a bond, —($C_1$-$C_4$)alkyl-O—, —O-($C_1$-$C_4$)alkyl, —($C_1$-$C_4$) alkyl-, —C(O)—, —C(O)NH—, or —NHC(O)—;

the A-ring is aryl selected from the group consisting of phenyl, naphthyl and fluorenyl, each of which is optionally substituted with 1, 2, or 3 groups that are independently, halogen, $C_1$-$C_4$ alkyl, $C_1$-$C_4$ alkoxy, $C_1$-$C_4$ haloalkyl, $C_1$-$C_4$ haloalkoxy, NO$_2$, NH$_2$, NH($C_1$-$C_6$)alkyl, N($C_1$-$C_6$)alkyl($C_1$-$C_6$)alkyl;

Q is pyrido [1,2-a]indolyl, indolyl, isoindolyl, indolizinyl, imidazo[1,2-a]pyridine, -phenyl-C(O)-phenyl, -phenyl-($C_1$-$C_4$) alkyl-phenyl, -pyridyl-phenyl, fluorenyl, oxofluorenyl, -fluorenyl-pyridyl, -fluorenyl-phenyl, -benzimidazolyl-($C_1$-$C_4$) alkyl-phenyl, benzoxazolyl-($C_1$-$C_4$) alkyl-phenyl, indolizinyl, -indolyl-($C_1$-$C_4$)alkyl-phenyl, -phenyl-benzoxazolyl, dibenzo[b,d]furanyl, or dibenzothienyl, each of which is optionally substituted with 1, 2, 3, or 4 groups that are independently $C_1$-$C_6$ alkyl, $C_1$-$C_4$ alkoxycarbonyl, $C_1$-$C_6$ alkoxy, halogen, haloalkyl, haloalkoxy, NR$_6$R$_7$, or phenyl; wherein $R_6$ and $R_7$ are independently H, $C_1$-$C_6$ alkyl, aryl($C_1$-$C_6$)alkyl, alkanoyl, phenyl($C_1$-$C_4$)alkanoyl, alkoxycarbonyl, phenyl($C_1$-$C_4$)alkoxycarbonyl, pyridylcarbonyl, pyridyl, piperidinyl, pyrrolidinylcarbonyl, —C(O)NH$_2$, —C(O)NH($C_1$-$C_6$)alkyl, —C(O)N($C_1$-$C_6$)alkyl ($C_1$-$C_6$)alkyl, or —SO$_2$-phenyl, wherein the cyclic groups are optionally substituted with 1, 2, 3, or 4 groups that are independently halogen, $C_1$-$C_4$ alkyl, $C_1$-$C_4$ alkoxy, NO$_2$, OH, NH$_2$, NH($C_1$-$C_6$) alkyl, N($C_1$-$C_6$)alkyl($C_1$-$C_6$)alkyl, CF$_3$ or OCF$_3$.

2. A compound according to claim 1, wherein the A-ring is selected from phenyl, or naphthyl, each of which is optionally substituted with 1, 2, or 3 groups that are independently, halogen, $C_1$-$C_4$ alkyl, $C_1$-$C_4$ alkoxy, $C_1$-$C_4$ haloalkyl, $C_1$-$C_4$ haloalkoxy, NO$_2$, NH$_2$, NH($C_1$-$C_6$)alkyl, or N($C_1$-$C_6$)alkyl ($C_1$-$C_6$)alkyl; and $R_{20}$, $R_{21}$, $R_{22}$, and $R_{23}$ are independently H, phenylalkoxy, phenylalkyl, halogen, alkyl, CF$_3$, OH, alkoxy, NO$_2$, NH$_2$, NH($C_1$-$C_6$)alkyl, N($C_1$-$C_6$)alkyl($C_1$-$C_6$) alkyl, NH-phenyl, NHC(O)—($C_1$-$C_4$) alkyl-phenyl, N($C_1$-$C_4$ alkyl)C(O)-($C_1$-$C_4$) alkyl-phenyl, N($C_1$-$C_4$) alkyl-phenyl, —NHSO$_2$-phenyl, or —N($C_1$-$C_4$alkyl) SO$_2$phenyl, wherein the phenyl groups are optionally substituted with 1, 2, 3, or 4 groups that are independently $C_1$-$C_6$ alkyl, $C_1$-$C_6$ alkoxy, halogen, OH, NO$_2$, $C_1$-$C_2$ haloalkyl, or $C_1$-$C_2$ haloalkoxy.

3. A compound according to claim 2, of the formula

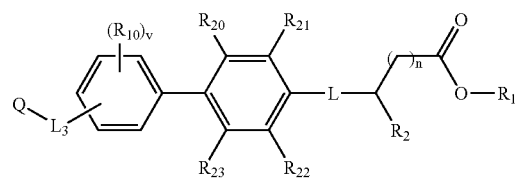

wherein

R₁ is H or C₁-C₆ alkyl;

R₂ is phenyl, phenyl(C₁-C₄) alkyl, C₁-C₆ alkyl, —(C₁-C₄) alkyl-C(O)NH₂, —(C₁-C₄) alkyl-S(O)ᵦ-(C₁-C₄) alkyl, or (C₁-C₄) hydroxyalkyl, wherein the phenyl groups are optionally substituted with 1, 2, 3, or 4 groups that are independently halogen, C₁-C₄ alkyl, C₁-C₄ alkoxy, —SO₂—(C₁-C₄) alkyl, (C₁-C₄)haloalkyl, or (C₁C₄) haloalkoxy;

v is 0, 1, 2, 3, or 4;

R₁₀ at each occurrence is independently halogen, C₁-C₄ alkyl, C₁-C₄ alkoxy, C₁-C₄ haloalkyl, C₁-C₄ haloalkoxy, NO₂, NH₂, NH(C₁-C₆)alkyl, or N(C₁-C₆) alkyl(C₁-C₆)alkyl; and L₃ is a bond, —O—(C₁-C₄)alkyl, —(C₁-C₄) alkyl-, or —C(O)—.

4. A compound according to claim 3, wherein

Q is pyrido[1,2-a]indolyl, indolyl, imidazo[1,2-a]pyridine, -phenyl-C(O)-phenyl, -phenyl-(C₁-C₄) alkyl-phenyl, fluorenyl, indolizinyl, -indolyl-(C₁-C₄)alkyl-phenyl, -phenyl-benzoxazolyl, dibenzo[b,d]furanyl, or dibenzothienyl, each of which is optionally substituted with 1, 2, 3, or 4 groups that are independently C₁-C₆ alkyl, C₁-C₄ alkoxycarbonyl, C₁-C₆ alkoxy, halogen, haloalkyl, haloalkoxy, NR₆R₇, or phenyl; wherein R₆ and R₇ are independently H, C₁-C₆ alkyl, aryl(C₁-C₆)alkyl, alkanoyl, phenyl(C₁-C₄)alkanoyl, alkoxycarbonyl, phenyl(C₁-C₄)alkoxycarbonyl, pyridylcarbonyl, pyridyl, pyrrolidinylcarbonyl, or —SO₂-phenyl, wherein the cyclic groups are optionally substituted with 1, 2, 3, or 4 groups that are independently halogen, C₁-C₄ alkyl, C₁-C₄ alkoxy, NO₂, OH, NH₂, NH(C₁-C₆)alkyl, N(C₁-C₆)alkyl (C₁-C₆) alkyl, CF₃ or OCF₃.

5. A compound according to claim 4, wherein

R₂ is phenyl, phenyl(C₁-C₄) alkyl, or (C₁-C₆)alkyl, wherein the phenyl groups are optionally substituted with 1, 2, 3, or 4 groups that are independently halogen, C₁-C₄ alkyl, C₁-C₄ alkoxy, or —SO₂—(C₁-C₄) alkyl, CF₃ or OCF₃; and R₂₀, R₂₁, R₂₂, and R₂₃ are independently selected from H, halogen, alkyl, OH, alkoxy, NO₂, NH₂, NH(C₁-C₆) alkyl, or N(C₁-C₆alkyl)(C₁-C₆alkyl).

6. A compound according to claim 5, wherein

L₃ is a bond, —O—(C₁-C₄)alkyl, —(C₁-C₄) alkyl-, or —C(O)—;

Q is indolyl, -phenyl-C(O)-phenyl, indolizinyl, -indolyl-(C₁-C₄)alkyl-phenyl, dibenzo[b,d]furanyl, or dibenzothienyl, each of which is optionally substituted with 1, 2, 3, or 4 groups that are independently C₁-C₆ alkyl, C₁-C₄ alkoxycarbonyl, C₁-C₆ alkoxy, halogen, haloalkyl, haloalkoxy, NR₆R₇, or phenyl; wherein R₆ and R₇ are independently H, C₁-C₆ alkyl, phenyl (C₁-C₆)alkyl, alkanoyl, phenyl(C₁-C₄)alkanoyl, alkoxycarbonyl, pyridylcarbonyl, pyridyl, pyrrolidinylcarbonyl, or —SO₂-phenyl, wherein the cyclic groups are optionally substituted with 1, 2, 3, or 4 groups that are independently halogen, C₁-C₄ alkyl, C₁-C₄ alkoxy, NO₂, OH, NH₂, NH(C₁-C₆)alkyl, N(C₁-C₆)alkyl(C₁-C₆)alkyl, CF₃ or OCF₃.

7. A compound according to claim 6 of the formula:

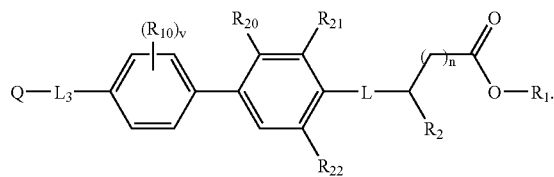

8. A compound according to claim 7, wherein

R₁ is H;

R₂₁ is H, NO₂, C₁-C₆ alkyl, or halogen; and

R₂ is phenyl, phenyl(C₁-C₄)alkyl, or (C₁-C₆)alkyl, wherein each phenyl group is optionally substituted with 1, 2, 3, or 4 groups that are independently halogen, C₁-C₄ alkyl, C₁-C₄ alkoxy, or —SO₂—(C₁-C₄) alkyl, CF₃ or OCF₃.

9. A compound according to claim 8, wherein

L₃ is a bond, —O—(C₁-C₄)alkyl, or —(C₁-C₄) alkyl-;

Q is indolyl, -phenyl-C(O)-phenyl, indolizinyl, or -indolyl-(C₁-C₄)alkyl-phenyl, each of which is optionally substituted with 1, 2, 3, or 4 groups that are independently C₁-C₆ alkyl, C₁-C₄ alkoxycarbonyl, C₁-C₆ alkoxy, halogen, haloalkyl, haloalkoxy, NR₆R₇, or phenyl; wherein R₆ and R₇ are independently H, C₁-C₆ alkyl, phenyl (C₁-C₆)alkyl, alkanoyl, phenyl(C₁-C₄)alkanoyl, alkoxycarbonyl, pyridylcarbonyl, pyrrolidinylcarbonyl, or —SO₂-phenyl, wherein the cyclic groups are optionally substituted with 1, 2, 3, or 4 groups that are independently halogen, C₁-C₄ alkyl, C₁-C₄ alkoxy, NO₂, OH, NH₂, NH(C₁-C₆)alkyl, N(C₁-C₆) alkyl (C₁-C₆)alkyl, CF₃ or OCF₃.

10. A compound according to claim 1 selected from the group consisting of ({4'-[3-(benzylamino)imidazo[1,2-a]pyridin-2-yl]biphenyl-4-yl}oxy)(phenyl)acetic acid;

{[4'-(5-methyl-1H-indol-1-yl)biphenyl-4-yl]oxy}(phenyl)acetic acid;

({4'-[3-(butylamino)imidazo[1,2-a]pyridin-2-yl]biphenyl-4-yl}oxy)(phenyl)acetic acid;

methyl ({4-[(2-benzoylphenoxy)methyl]biphenyl-4-yl}oxy)(phenyl)acetate;

methyl ({4'-[(2-benzylphenoxy)methyl]biphenyl-4-yl}oxy)(phenyl)acetate;

methyl ({4'-[(9H-fluoren-2-yloxy)methyl]biphenyl-4-yl}oxy)(phenyl)acetate;

methyl ({4'-[(3-benzoylphenoxy)methyl]biphenyl-4-yl}oxy)(phenyl)acetate;

({4'-[(3-benzoylphenoxy)methyl]biphenyl-4-yl}oxy) (phenyl)acetic acid;

({4'-[(2-benzoylphenoxy)methyl]biphenyl-4-yl}oxy) (phenyl)acetic acid;

{[4'-(1-butylindolizin-2-yl)biphenyl-4-yl]oxy}(phenyl) acetic acid;

({4'-[10-(ethoxycarbonyl)pyrido[1,2-a]indol-3-yl]biphenyl-4-yl}oxy)(phenyl)acetic acid;

{[4'-(1H-indol-1-yl)biphenyl-4-yl]oxy}(phenyl)acetic acid;

methyl {[4'-(1-benzyl-1H-indol-6-yl)biphenyl-4-yl]oxy} (phenyl)acetate;

{[4'-(1-benzyl-1H-indol-6-yl)biphenyl-4-yl]oxy}(phenyl)acetic acid;

({[4'-(1-benzyl-1H-indol-5-yl)biphenyl-4-yl]oxy}(phenyl)acetic acid;

2-{[4'-(1-butylindolizin-2-yl)biphenyl-4-yl]oxy}propanoic acid;

(2R)-2-{[4-(1-butylindolizin-2-yl)biphenyl-4-yl]oxy}-3-phenylpropanoic acid;

(2S)-2-{[4-(1-butylindolizin-2-yl)biphenyl-4-yl]oxy}-4-phenylbutanoic acid;

{[2''-(1,3-benzoxazol-2-yl)-1,1':4',1''-terphenyl-4-yl]oxy}(phenyl)acetic acid;

[(4'-dibenzo[b,d]furan-4-ylbiphenyl-4-yl)oxy](phenyl)acetic acid;

[(4'-{[(9-oxo-9H-fluoren-1-yl)oxy]methyl}biphenyl-4-yl)oxy](phenyl) acetic acid;

methyl {[4'-(1-benzyl-1H-indol-5-yl)biphenyl-4-yl]oxy}(phenyl)acetate;

[(4'-dibenzo[b,d]thien-4-ylbiphenyl-4-yl)oxy](phenyl)acetic acid;

[4'-(5-Chloro-indol-1-yl)-biphenyl-4-yloxy]-phenyl-acetic acid;

(3-Chloro-4'-dibenzofuran-4-yl-biphenyl-4-yloxy)-phenyl-acetic acid;

(4'-Dibenzofuran-4-yl-2-methyl-biphenyl-4-yloxy)-phenyl-acetic acid;

(4'-Dibenzofuran-4-yl-3-fluoro-biphenyl-4-yloxy)-phenyl-acetic acid;

(2-Chloro-4'-dibenzofuran-4-yl-biphenyl-4-yloxy)-phenyl-acetic acid; and (4'-Dibenzofuran-4-yl-2-trifluoromethyl-biphenyl-4-yloxy)-phenyl-acetic acid.

11. A compound selected from the group consisting of

{[4'-(1-benzofuran-2-yl)biphenyl-4-yl]oxy}(phenyl)acetic acid;

({4'-[(2-butyl-1-benzofuran-3-yl)carbonyl]biphenyl-4-yl}oxy)(phenyl)acetic acid;

{[4'-(1-benzothien-2-yl)biphenyl-4-yl]oxy}(phenyl)acetic acid;

[(4''-butyl-1,1':4',1''-terphenyl-4-yl)oxy](phenyl)acetic acid;

({4'-[(2-benzyl-7-fluoro-1-benzofuran-3-yl)carbonyl]biphenyl-4-yl}oxy)(phenyl)acetic acid; and methyl {[4'-(1-benzofuran-2-yl)biphenyl-4-yl]oxy}(phenyl)acetate.

\* \* \* \* \*

SEQUENCE LISTING

<160> NUMBER OF SEQ ID NOS: 1

<210> SEQ ID NO 1
<211> LENGTH: 12
<212> TYPE: PRT
<213> ORGANISM: Artificial sequence

```
<220> FEATURE:
<223> OTHER INFORMATION: synthetic peptide
<220> FEATURE:
<221> NAME/KEY: MISC_FEATURE
<222> LOCATION: (5)..(5)
<223> OTHER INFORMATION: phosphotyrosine
<220> FEATURE:
<221> NAME/KEY: MISC_FEATURE
<222> LOCATION: (9)..(10)
<223> OTHER INFORMATION: phosphotyrosine

<400> SEQUENCE: 1

Thr Arg Asp Ile Tyr Glu Thr Asp Tyr Tyr Arg Lys
1               5                   10
```